United States Patent
Ebi et al.

(10) Patent No.: US 10,208,352 B2
(45) Date of Patent: *Feb. 19, 2019

(54) PROVIDING CERVICAL OR ORAL MUCOSA CANCERATION INFORMATION FROM MEASUREMENT OF CELLS LOCATED TOWARD THE BASAL MEMBRANE SIDE OF EPITHELIAL TISSUE

(71) Applicant: Sysmex Corporation, Kobe-shi, Hyogo (JP)

(72) Inventors: Ryuichiro Ebi, Kobe (JP); Koki Tajima, Kobe (JP); Shigeki Abe, Kobe (JP); Masanori Kawano, Kobe (JP)

(73) Assignee: SYSMEX CORPORATION, Kobe (JP)

( * ) Notice: Subject to any disclaimer, the term of this patent is extended or adjusted under 35 U.S.C. 154(b) by 98 days.

This patent is subject to a terminal disclaimer.

(21) Appl. No.: 14/159,924

(22) Filed: Jan. 21, 2014

(65) Prior Publication Data

US 2014/0199702 A1   Jul. 17, 2014

Related U.S. Application Data

(63) Continuation of application No. PCT/JP2012/067128, filed on Jul. 4, 2012.

(30) Foreign Application Priority Data

Jul. 22, 2011   (JP) ................................ 2011-160746

(51) Int. Cl.
   *C12Q 1/6886*   (2018.01)
   *G01N 33/574*   (2006.01)
   *G01N 15/14*   (2006.01)

(52) U.S. Cl.
   CPC ......... *C12Q 1/6886* (2013.01); *G01N 33/574* (2013.01); *G01N 15/1459* (2013.01)

(58) Field of Classification Search
   None
   See application file for complete search history.

(56) References Cited

U.S. PATENT DOCUMENTS

| | | | |
|---|---|---|---|
| 2005/0221399 A1 | 10/2005 | Nakano et al. | |
| 2008/0108103 A1 | 5/2008 | Ishisaka et al. | |
| 2008/0317325 A1* | 12/2008 | Ortyn | G01N 15/147 |
| | | | 382/133 |
| 2009/0091746 A1 | 4/2009 | Fukuda et al. | |
| 2011/0014646 A1 | 1/2011 | Fukuda et al. | |
| 2011/0014685 A1 | 1/2011 | Fukuda et al. | |

FOREIGN PATENT DOCUMENTS

| | | |
|---|---|---|
| JP | 2004-286666 A | 10/2004 |
| JP | 2005-315862 A | 11/2005 |
| JP | 2009-103687 A | 5/2009 |
| WO | WO 2006/103920 A1 | 10/2006 |
| WO | WO 2009/122999 A1 | 10/2009 |

OTHER PUBLICATIONS

Park, "Large liver cell dysplasia: a controversial entity," Journal of hepatology, vol. 45, p. 734-743, 2006.*
Watanabe, "Morphologic studies of the liver cell dysplasia," Cancer, vol. 51, p. 2197-2205, 1983.*
El-Sayed, "DNA ploidy and liver cell dysplasia in liver biopsies from patients with liver cirrhosis," Canadian journal of gastroenterology, vol. 18, p. 87-91, 2004.*
Gong, "Simultaneous analysis of cell cycle kinetics at two different DNA ploidy levels based on DNA content and cyclin B measurements," Cancer research, vol. 53, p. 5096-5099, 1993.*
Vermes, "Flow cytometry of apoptotic cell death," Journal of immunological methods, vol. 243(1), p. 167-190, 2000.*
Han, "A novel highly sensitive and specific flow cytometry system for cervical cancer screening," Gynecologic oncology, vol. 139(1), p. 52-58, 2015.*
Cibas, "Cervical and Vaginal Cytology," In: Cytology: Diagnostic principles and clinical correlates, 3rd Edition, Saunders, an imprint of Elsevier, Philadelphia, PA, p. 1-36, 2009.*
Unknown author, "Diagnosis, Treatment and Management of Gynecological Diseases," Acta Obstetrica et Gynaecologica Japonica, vol. 61, No. 4, 2009, pp. N102-N105.
International Search Report for International Application No. PCT/JP2012/067128, dated Aug. 7, 2012, 2 pages.
Unknown author, "Diagnosis, Treatment and Management of Gynecological Diseases," Acta Obstetrica et Gynaecologica Japonica, vol. 61, No. 4, 2009, pp. N102-N106 (full English translation).
Shah et al., "Morphometric Pattern Analysis of Basal Cell Nuclei for Oral Cancer Screening", Bioinformatics and Biomedical Engineering (ICBBE), 2010 4th International Conference on IEEE, Jun. 18, 2010, pp. 1-4.
Jusman et al., "Intelligent Screening Systems for Cervical Cancer", The Scientific World Journal, vol. 4115, No. 3, Jan. 1, 2014, pp. 1-15.

* cited by examiner

Primary Examiner — G Steven Vanni
(74) Attorney, Agent, or Firm — Brinks Gilson & Lione

(57) ABSTRACT

There is provided a canceration information providing method which can detect the possibility of cancer in the initial stage with high accuracy. The canceration information providing method for providing information pertaining to canceration of cells includes: acquiring measurement data including first data pertaining to size of a cell nucleus and second data pertaining to size of a cytoplasm for each cell contained in a measurement sample which includes cells collected from epithelial tissue; extracting the measurement data of cells to be analyzed, which are at least some of the cells located toward the basal membrane side of the cells existing in the surface layer in the epithelial tissue, from the measurement data of a plurality of cells in the measurement sample based on the first data and the second data acquired for each cell; and analyzing the extracted measurement data and outputting the information pertaining to the canceration of cells.

18 Claims, 20 Drawing Sheets

PROVIDING CERVICAL OR ORAL MUCOSA CANCERATION INFORMATION FROM MEASUREMENT OF CELLS LOCATED TOWARD THE BASAL MEMBRANE SIDE OF EPITHELIAL TISSUE

RELATED APPLICATIONS

This application is a continuation of PCT/JP2012/067128 filed on Jul. 4, 2012, which claims priority to Japanese Application No. 2011-160746 filed on Jul. 22, 2011. The entire contents of these applications are incorporated herein by reference.

FIELD OF THE INVENTION

The present invention relates to a canceration information providing method, which analyzes cells and provides information pertaining to canceration of the cells, and a canceration information providing device.

BACKGROUND OF THE INVENTION

An analyzer for automatically analyzing the cells of a subject and providing information pertaining to canceration of the cells is known (for example, refer to US Patent Application publication No. 2008/0108103 and Japanese Patent Laid-open Publication No. 2004-286666). US Patent Application publication No. 2008/0108103 discloses a device that flows a measurement sample including cells collected from a subject to a flow cell, irradiates the measurement sample flowing through the flow cell with light to acquire a scattered light signal for the individual cell, extracts a characteristic parameter by analyzing the waveform of each scattered light signal, and discriminates cancer/atypical cell from a plurality of cells using the characteristic parameter.

Japanese Patent Laid-open Publication No. 2004-286666 discloses a device for supporting pathological diagnosis: capturing an image of cells flowing through a flow cell; estimating the distribution of the nucleus and cytoplasm from the acquired image data; and estimating the distribution of cancer sites in a pathological specimen based on a ratio (N/C ratio) of the area of the estimated distribution of the nucleus and cytoplasm.

For example, in the tissue diagnosis of the uterine cervix, the process from the normal state to cancer has a plurality of stages, "Normal", "CIN1", "CIN2", "CIN3", and "Cancer" in order from the normal state. Among them, the stages, "CIN1", "CIN2", and "CIN3 " are in the stage called "cervical intraepithelial neoplasia (CIN)".

"CIN1" is a state in which the atypical parabasal cells are growing in one third from a basal layer to a surface layer, and is a state in which the possibility of regressing spontaneously is high. Thus, treatment is determined as unnecessary in "CIN1". "CIN2" is a state in which the atypical parabasal cells are growing in two thirds from the basal layer to the surface layer. Treatment is determined as necessary in "CIN2". "CIN3" is a state in which the atypical parabasal cells are growing entirely from the basal layer to the surface layer. Treatment is determined as necessary in "CIN3". In order to start the treatment for cancer in the initial stage, it is preferable to detect the possibility of cancer in the initial stages of cancer such as "CIN2" and "CIN3 " before the stage "Cancer". It is preferable to distinguish between the cell in the stage before the stage "CIN1" determined as unnecessary for the treatment and the cell in the stage after the stage "CIN2" determined as necessary for the treatment.

In the stage "CIN1" determined as unnecessary for the treatment or the stage "CIN2" determined as necessary for the treatment, the normal cells, cancer cells or atypical cells are mixed. Thus, even if the cells are collected from the uterine cervix of a subject of "CIN1" to prepare a measurement sample or the cells are collected from the uterine cervix of a subject of "CIN2" to prepare a measurement sample, the normal cells, cancer cells or atypical cells are mixed in both of the measurement samples. Even if only the atypical cells are detected, it is difficult to detect the possibility of cancer in the initial stage with high accuracy.

Even if a measurement sample prepared by collecting from the uterine cervix of a subject in the initial stage of cancer is analyzed by the analyzer described in US Patent Application publication No. 2008/0108103 and Japanese Patent Laid-open Publication No. 2004-286666, a percentage of the cancer cells or atypical cells in the total number of the cells to be analyzed is decreased. Thus, it is difficult to detect the possibility of cancer in the initial stage with high accuracy.

SUMMARY OF THE INVENTION

The scope of the present invention is defined solely by the appended claims, and is not affected to any degree by the statements within this summary.

A first aspect of the present invention is a canceration information providing method for providing information pertaining to canceration of cells, comprising:

acquiring measurement data including first data pertaining to size of a cell nucleus and second data pertaining to size of a cytoplasm for each cell contained in a measurement sample which includes cells collected from epithelial tissue;

extracting the measurement data of cells to be analyzed, which are at least some of the cells located toward the basal membrane side of the cells existing in the surface layer in the epithelial tissue, from the measurement data of a plurality of cells in the measurement sample based on the first data and the second data acquired for each cell; and analyzing the extracted measurement data and outputting the information pertaining to the canceration of cells.

A second aspect of the present invention is an canceration information providing device for providing information pertaining to canceration of cells, comprising:

a data acquiring unit which acquires measurement data including first data pertaining to size of a cell nucleus and second data pertaining to size of a cytoplasm for each cell contained in a measurement sample which includes cells collected from epithelial tissue; and a processor programmed to execute a computer program that enables the processor to:

extract the measurement data of cells to be analyzed, which are at least some of the cells located toward the basal membrane side of the cells existing in the surface layer in the epithelial tissue, from the measurement data of a plurality of cells in the measurement sample based on the first data and the second data acquired for each cell;

analyze the extracted measurement data; and output the information pertaining to the canceration of cells.

DETAILED DESCRIPTION OF THE PREFERRED EMBODIMENTS

The preferred embodiments of the present invention will be described hereinafter with reference to the drawings.

Hereinafter, embodiments of the canceration information providing device and the canceration information providing method of the present invention will be particularly described with reference to the drawings.

[Whole Configuration of Canceration Information Providing Device]

Figure 1:
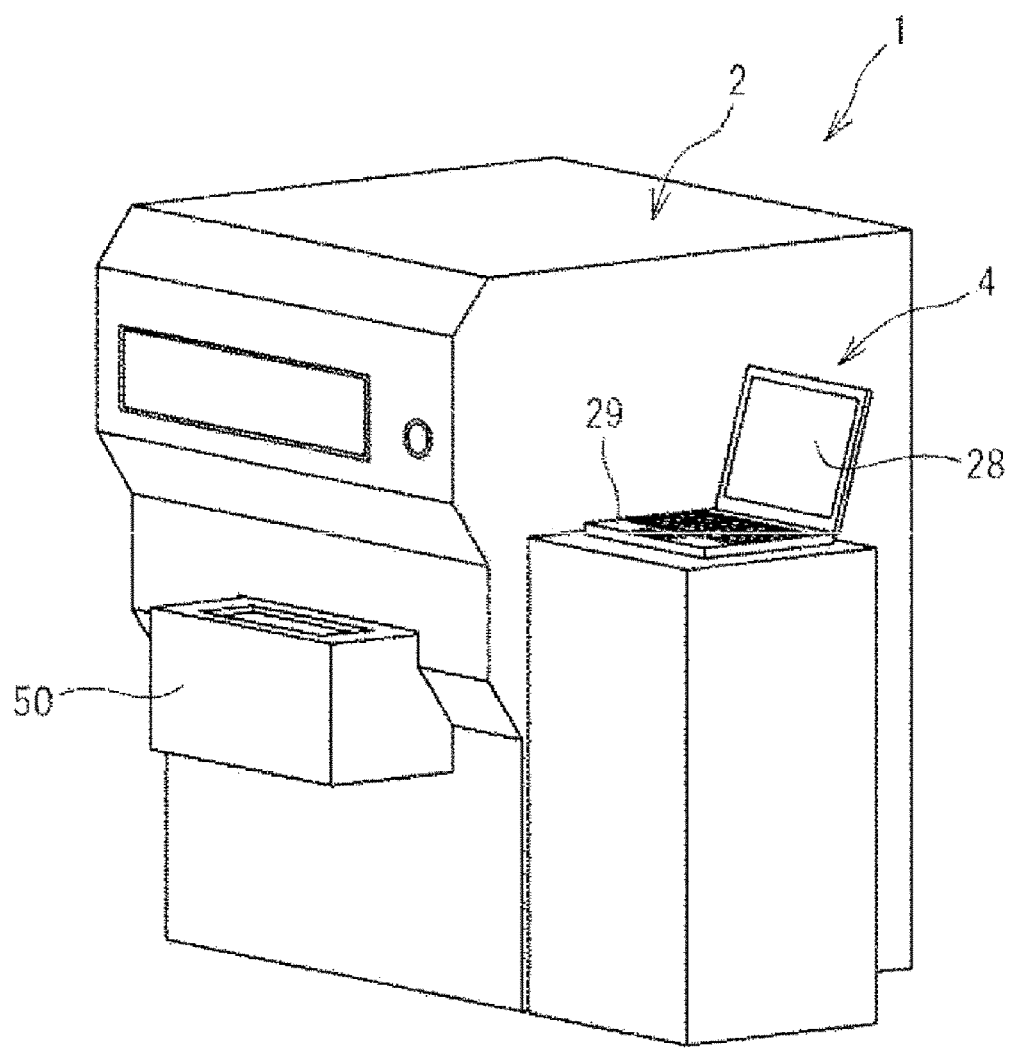
FIG. 1 is a perspective explanatory view of a canceration information providing device according to one embodiment of the present invention.

A canceration information providing device 1 shown in FIG. 1 or FIG. 2 determines whether or not cancerous cells or cells in the process of canceration (hereinafter, collectively referred to as "cancerous cells") are included by flowing a measurement sample containing cells collected from patients (subjects) to a flow cell, irradiating the measurement sample flowing through the flow cell with a laser light, and detecting and analyzing light from the measurement sample (e.g. forward scattered light and side fluorescence), and outputs the result. Specifically, the canceration information providing device 1 is used to screen cervical cancer using epithelial cells of the uterine cervix collected from the patients. The canceration information providing device 1 comprises a measurement device 2 which measures a sample and a data processing device 4 which is connected to the measurement device 2 and analyzes and displays (outputs) the measurement result. As shown in FIG. 1, the canceration information providing device 1 further includes a sample setting unit 50 for setting a plurality of test tubes (not shown) which hold a mixed solution of a preservative solution containing methanol as a main component and a biological sample collected from a patient.

Figure 2:
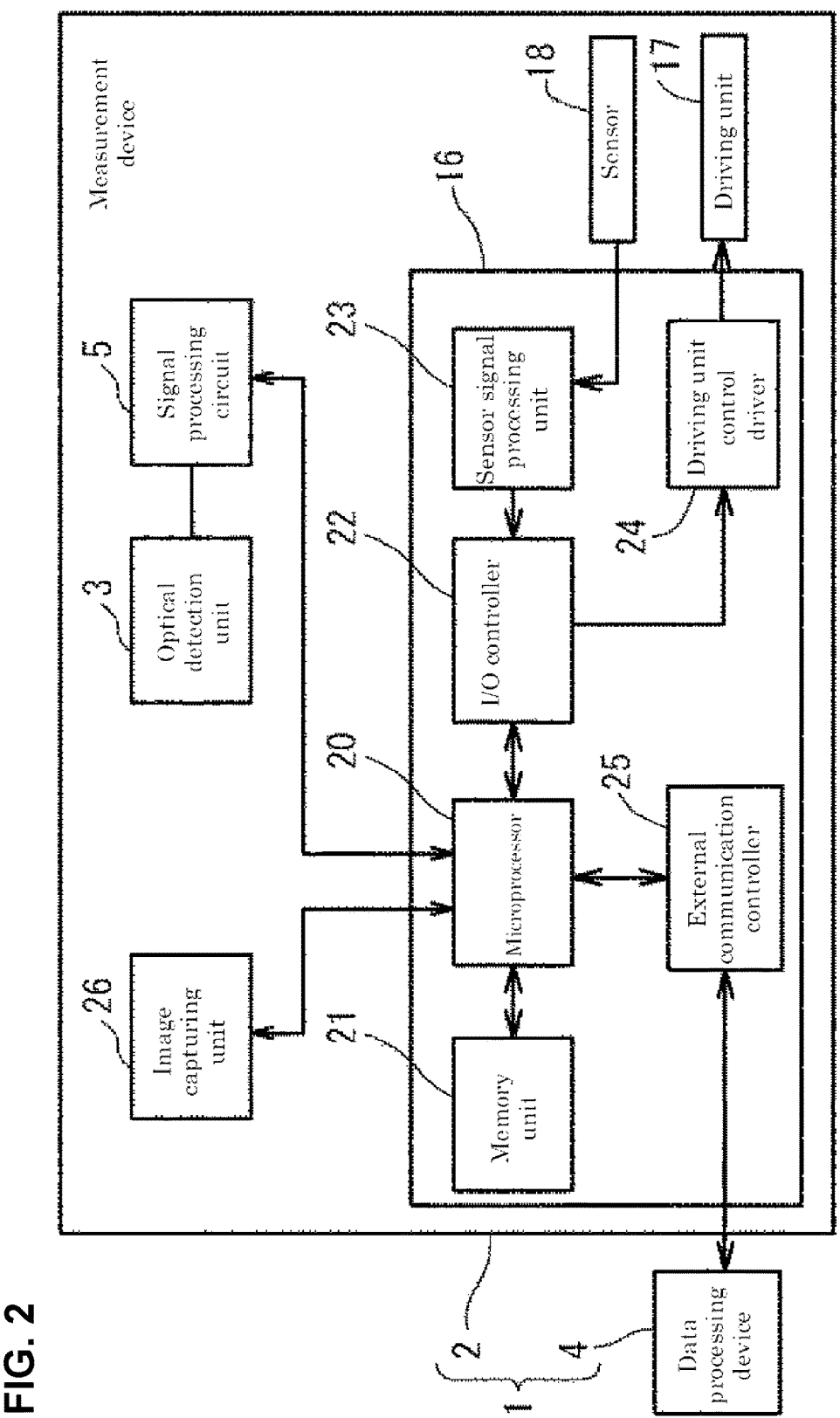
FIG. 2 is a block diagram showing a configuration of the canceration information providing device shown in FIG. 1.

As shown in FIG. 2, the measurement device 2 of the canceration information providing device 1 comprises an optical detection unit 3 including a flow cytometer, which is an optical information acquiring unit for detecting information such as cells and the size of nucleus from the measurement sample, a signal processing circuit 5, a measurement control unit 16, a driving unit 17 including a motor, an actuator, and a valve, various sensors 18, and an image capturing unit 26 which captures images of cells. The signal processing circuit 5 comprises an analog signal processing circuit which subjects the output from a flow cytometer 3 amplified by a preamplifier (not shown) to an amplification or filter processing, an A/D converter which converts the output from the analog signal processing circuit to a digital signal, and a digital signal processing circuit which subjects the digital signal to a predetermined waveform processing. The measurement control unit 16 processes the signal of the sensor 18 and controls the operation of the driving unit 17 to aspirate and measure the measurement sample. When cervical cancer is screened, one prepared by subjecting cells collected from the uterine cervix (epithelial cells) of patients to centrifuging, diluting, stirring, and PI staining can be used as the measurement sample. The prepared measurement sample held in a test tube is disposed at a predetermined position of the sample setting unit 50. Subsequently, it is transported to the lower position of a pipette (not shown) of the measurement device 2 and aspirated by the pipette. The aspirated sample and a sheath solution are fed to the flow cell. Thus, a sample flow is formed in the flow cell. The PI staining (DNA staining) is performed with propidium iodide (PI) which is a fluorescent staining solution containing a red pigment. Since nuclei are selectively stained in the PI staining, the red fluorescence from the nuclei can be detected.

[Configuration of Measurement Control Unit]

The measurement control unit 16 comprises a microprocessor 20, a memory unit 21, an I/O controller 22, a sensor signal processing unit 23, a driving unit control driver 24, and an external communication controller 25. The memory unit 21 includes Read Only Memory (ROM), Random Access Memory (RAM), and the like. Control programs for controlling the driving unit 17 and data required for executing the control programs are stored in the ROM. The microprocessor 20 is capable of executing the control programs loaded in the RAM or directly executing the control programs in the ROM.

The signal from the sensor 18 is transmitted to the microprocessor 20 through the sensor signal processing unit 23 and the I/O controller 22. The microprocessor 20 executes the control programs to be able to control the driving unit 17 via the I/O controller 22 and the driving unit control driver 24 in response to the signal from the sensor 18. The data processed by the microprocessor 20 and the data necessary for the processing of the microprocessor 20 are transmitted and received with an external device such as the data processing device 4 via the external communication controller 25.

[Configuration of Data Processing Device]

Figure 3:
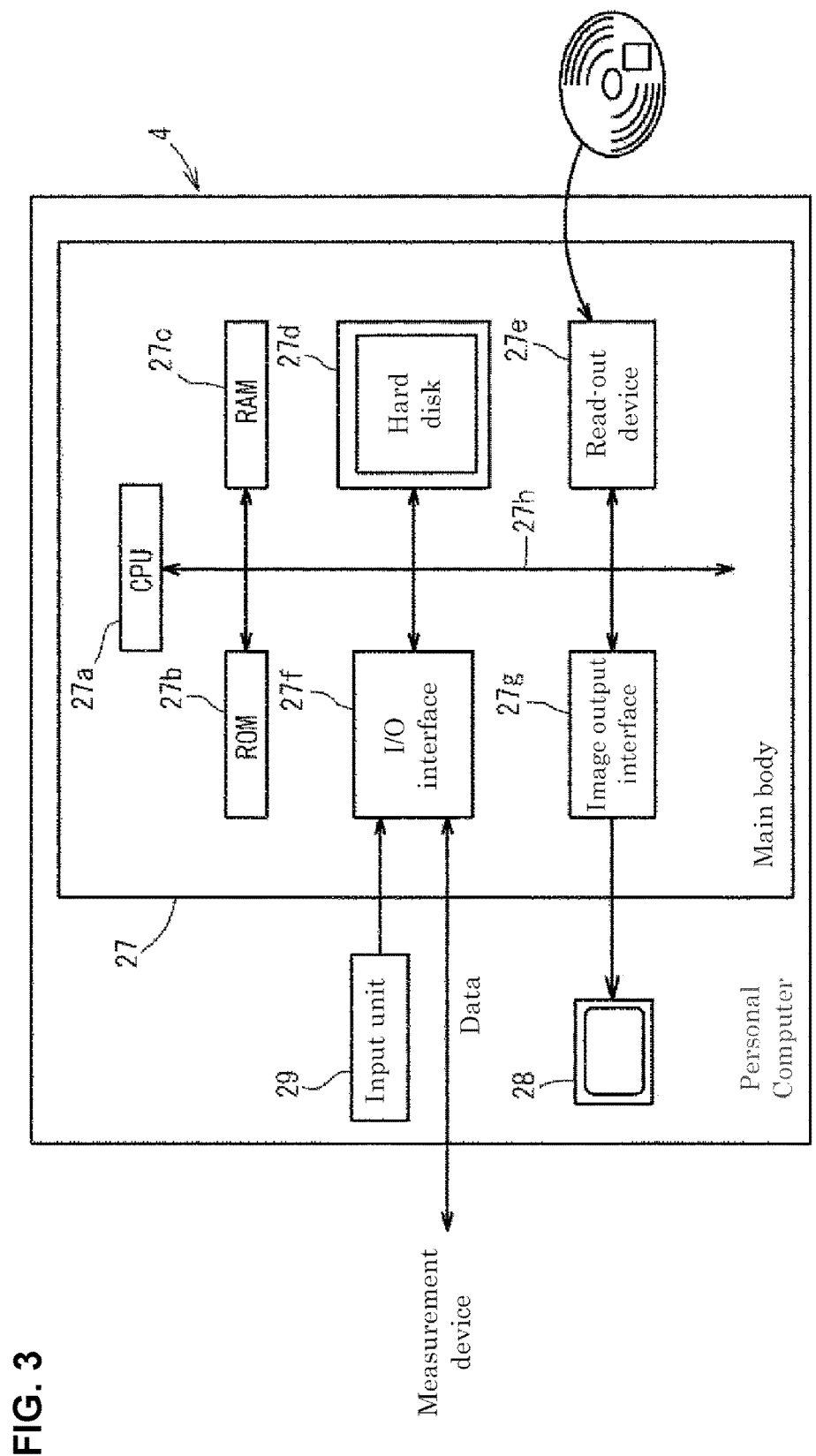
FIG. 3 is a block diagram of a personal computer which configures a data processing device in the canceration information providing device shown in FIG. 1.

As shown in FIG. 3, the data processing device 4 includes a personal computer, and the like and is mainly configured by a main body 27, a display unit 28, and an input unit 29.

The main body 27 is mainly configured by a Central Processing Unit 27a (CPU), a ROM 27b, a RAM 27c, a hard disk 27d, a read-out device 27e, an I/O interface 27f, and an image output interface 27g. Such components are communicably connected by a bus 27h.

The CPU 27a executes computer programs stored in the ROM 27b and the computer programs loaded in the RAM 27c. The CPU 27a serves as a data acquiring unit for acquiring the data of the size of the cell nucleus to be described below and the data of the size of cytoplasm or a control unit for analyzing the extracted cells and outputting information pertaining to canceration.

The ROM 27b is configured by mask ROM, PROM, EPROM, EEPROM, and the like, and stores computer programs to be executed by the CPU 27a and data used for the same. The RAM 27c is configured by SRAM, DRAM, and the like. The RAM 27c is used to read out the computer programs recorded on the ROM 27b and the hard disc 27d. In executing the computer program, the RAM 27c is used as a work region of the CPU 27a.

The hard disc 27d is installed with various computer programs to be executed by the CPU 27a such as operating system and application program, as well as data used in executing the computer program. For instance, operating system providing graphical user interface environment such as Windows (registered trademark) manufactured and sold by US Microsoft Co. is installed in the hard disc 27d. Further, a computer program for producing waveform data to be described below or calculating an N/C ratio and the data used in executing the computer program are installed in the hard disk 27d.

An operation program for performing transmission of a measurement order (operation command) to the measurement control unit 16 of the canceration information providing device 1, reception and processing of the measurement result measured in the measurement device 2, display of the processed analysis result, and the like is installed in the hard disk 27d. The operation program operates on the operating system.

The read-out device 27e is configured by flexible disc drive, CD-ROM drive, DVD-ROM drive, or the like, and is able to read out computer programs or data recorded on a portable recording medium. The I/O interface 27f is configured by serial interface such as USB, IEEE1394, RS-232C; parallel interface such as SCSI, IDE, IEEE1284; analog interface such as D/A converter, A/D converter, and the like. The input unit 29 such as keyboard and mouse is connected to the I/O interface 27f, so that the user can input data to the personal computer by operating the input unit 29. The I/O interface 27f is connected to the measurement device 2, and can transmit and receive data with the measurement device 2.

The image output interface 27g is connected to the display unit 28 configured by LCD, CRT, or the like, and is configured to output an image signal corresponding to the image data provided from the CPU 27a to the display unit 28. The display unit 28 displays an image (screen) in response to the input image signal and the waveform signal.

[Configuration of Flow Cytometer and Image Capturing Unit]

Figure 4:
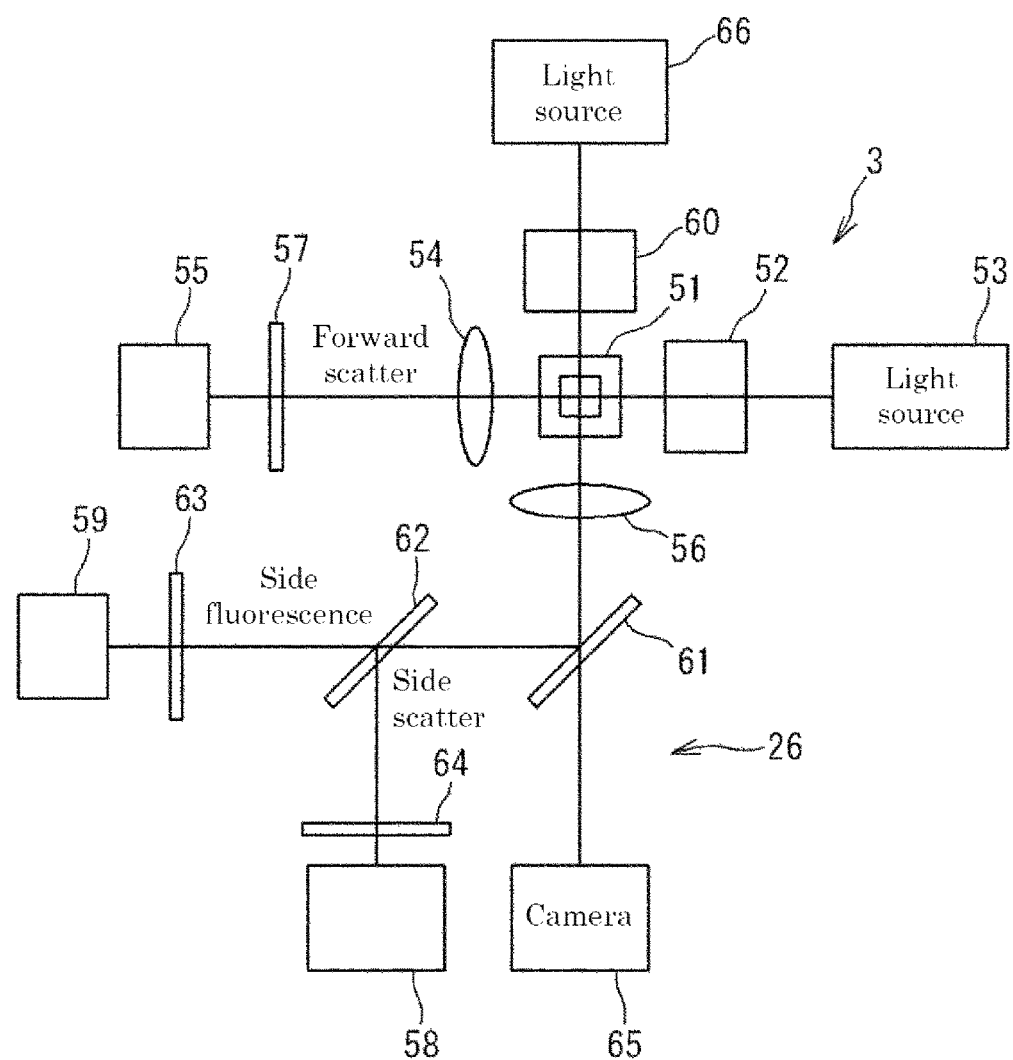
FIG. 4 is a block diagram showing a configuration of a flow cytometer in the canceration information providing device shown in FIG. 1.

FIG. 4 is a view showing the optical detection unit 3 including the optical information acquiring unit and the configuration of the image capturing unit 26. The optical detection unit 3 including a flow cytometer comprises a light source 53 including a semiconductor laser. A lens system 52 collects the laser light emitted from the light source 53 on the measurement sample flowing through the flow cell 51.

The forward scattered light generated from the cells in the measurement sample by the laser light is detected by a photodiode (light receiving unit) 55 through an objective lens 54 and a filter 57. The lens system 52 is configured by a lens group including a collimator lens, a cylinder lens, a condenser lens, and the like.

Further, the side fluorescence and side scattered light from the cells passes through the objective lens 56 disposed at the side of the flow cell 51 and enters a dichroic mirror 61. The side fluorescence and side scattered light reflected by the dichroic mirror 61 enters a dichroic mirror 62.

The side fluorescence that passes the dichroic mirror 62 also passes through a filter 63 and is detected by a photomultiplier 59. The side scattered light reflected by the dichroic mirror 62 passes through a filter 64 and is detected by a photomultiplier 58.

The photodiode 55, the photomultiplier 58, and the photomultiplier 59 convert the detected light to electrical signals and respectively output a forward scattered light signal (FSC), a side scattered light signal (SSC), and a side fluorescent signal (SFC). These signals are amplified by preamplifiers not shown in the drawing, and thereafter the amplified signals are transmitted to the signal processing circuit 5 (refer to FIG. 2).

As shown in FIG. 2, the signal processing circuit 5 performs signal processing such as filter processing and A/D conversion processing and the like to obtain the forward scattered light data, side scattered light data, and side fluorescence data. The above data are transmitted by the microprocessor 20 to the data processing device 4 via the external communication controller 25, where the data are stored on the hard disk 27d. In the data processing device 4, the width of cytoplasm or nucleus, the N/C ratio and the like are calculated based on the forward scattered light data, side scattered light data, and side fluorescence data.

As the light source 53, a gas laser can also be used in place of the semiconductor laser, and the semiconductor laser is preferably employed from the viewpoint of low cost, small size, and low power. Reduction of product cost as well as miniaturization and electric power saving of the device are achieved by using the semiconductor laser. In the present embodiment, a blue semiconductor laser with a short wavelength which has an advantage in narrowing the beam is used. The blue semiconductor laser is also effective for a fluorescence excitation wavelength such as PI. Among the semiconductor lasers, a red semiconductor laser having advantages of low cost, a long life, and the stable supply from manufacturers may be used as the light source 53.

In the present embodiment, the image capturing unit 26 is provided in addition to the flow cytometer 3. The image capturing unit 26 comprises a pulse laser light source 66 and a CCD camera 65 as shown in FIG. 4. The laser light from the pulse laser 66 passes through the lens system 60 and enters the flow cell 51, then passes through the objective lens 56 and the dichroic mirror 61 to form an image in the camera 65. The pulse laser 66 emits light with a predetermined timing so as to be able to form an image by the camera 65.

As shown in FIG. 2, the image of the cells captured by the camera 65 is transmitted by the microprocessor 20 to the data processing device 4 via the external communication controller 25. In the data processing device 4, the image of cells is then associated with the above described forward scattered light data, side scattered light data, and side fluorescence data and stored on the hard disk 27d according to the cells.

[Method for Providing Canceration Information]

Subsequently, an example of the flow of the canceration information providing method using the canceration information providing device 1 according to the present embodiment will be described with reference to FIG. 5.

In the analysis using the canceration information providing device 1, the user first removes aggregating cells from the cells (epithelial cells) collected from the uterine cervix of patients and performs pretreatment such as PI staining to prepare a measurement sample. Thereafter, the user set a test tube holding the pretreated measurement sample and the preservative solution containing methanol as a main component in the sample setting unit 50 to start the analysis by the canceration information providing device 1.

The removal of the aggregating cells is performed in order to prevent lowering of analysis accuracy that occurs when the measurement amount of DNA indicates an abnormal value when a plurality of cells aggregate although the amount of DNA is normal as a single cell. The removal of the aggregating cells can be performed by, for example, a combination processing of a dispersing operation comprising rotating a rotating rotation shaft disposed in a diluted biological sample by a motor to disperse cells in the biological sample and a filtering operation comprising passing the dispersed biological sample through a filter to remove the aggregating cells, a processing of applying ultrasonic vibrations to the biological sample or the like. In the latter case, the shock (pressure fluctuation) associated with the cavitation in the biological sample caused by ultrasonic vibrations (formation of fine air bubbles and rupture of the air bubbles) allows the aggregating cells to be dispersed.

Figure 5:
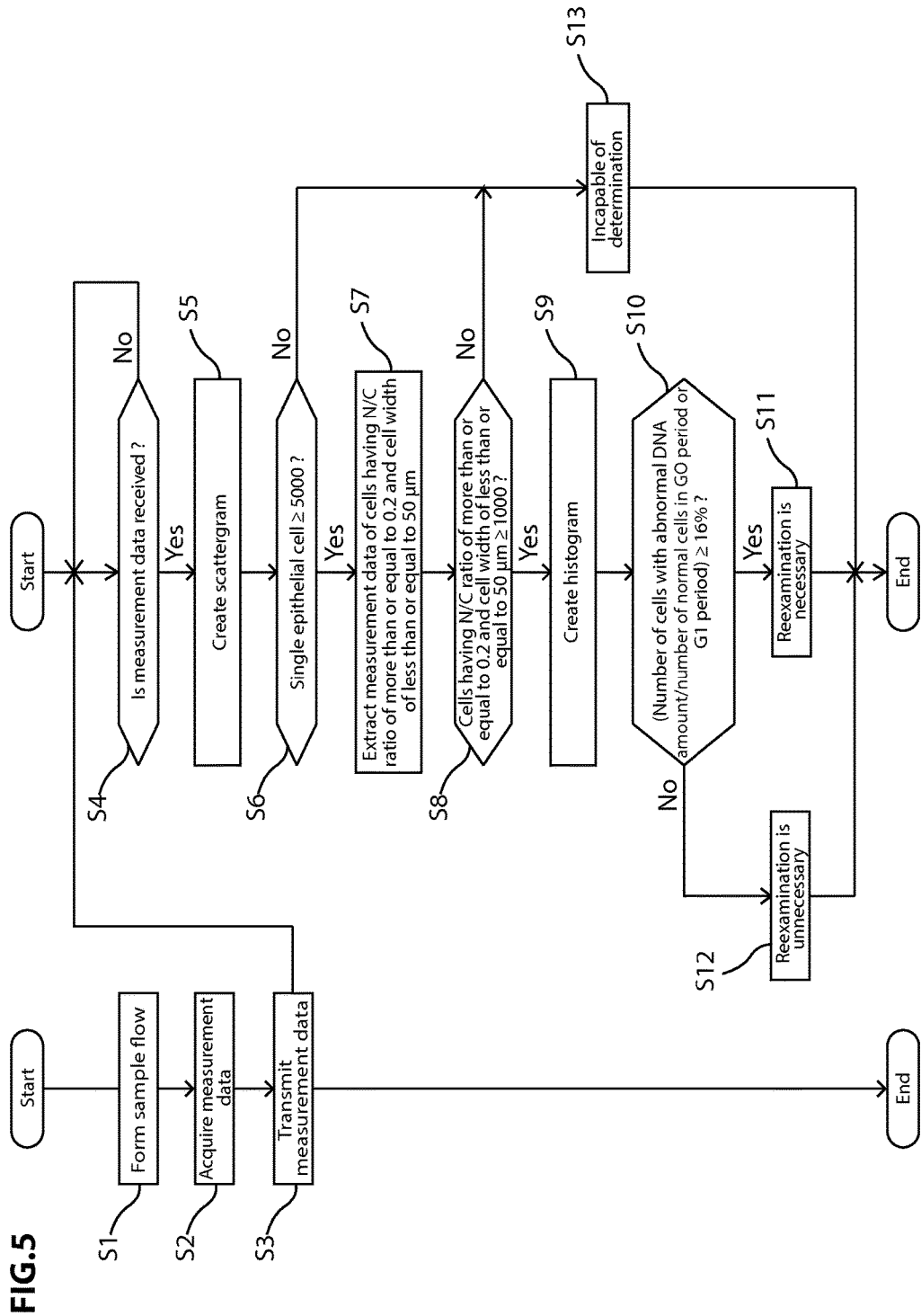
FIG. 5 is a flow chart showing an example of the flow of the canceration information providing method.

FIG. 5 is a flow chart showing the processing from when the user gives an instruction to start the measurement to the CPU 27a of the data processing device 4 to when canceration information is provided, which is executed by the microprocessor 20 of the measurement device 2 and the CPU 27a of the data processing device 4 of the canceration information providing device 1 according to this embodiment. The measurement start instruction by the user is performed after the data processing device 4 is powered on and the computer program stored in the data processing device 4 is initialized. When the user gives the instruction to start the measurement to the CPU 27a, the CPU 27a transmits the measurement start instruction to the microprocessor 20 of the measurement device 2. When the microprocessor 20 receives the measurement start instruction, in the measurement device 2, the measurement sample held in the test tube is aspirated by the pipette, fed to the flow cell 51 shown in FIG. 4, and a sample flow is formed (Step S1).

The cells in the measurement sample flowing through the flow cell 51 are irradiated with laser light, the forward scattered light from the cells is detected by the photodiode 55, the side scattered light is detected by the photomultiplier 58, and the side fluorescence is detected by the photomultiplier 59.

Then, the forward scattered light signal, side scattered light signal, and side fluorescent signal output from the flow cytometer 3 are transmitted to the signal processing circuit 5 and subjected to a predetermined processing by the signal processing circuit 5 so as to obtain the forward scattered light data showing forward scattered light intensity, side scattered light data showing side scattered light intensity, and side fluorescence data showing side fluorescent intensity as well as the characteristic parameter to be described below (Step S2).

Figure 6:
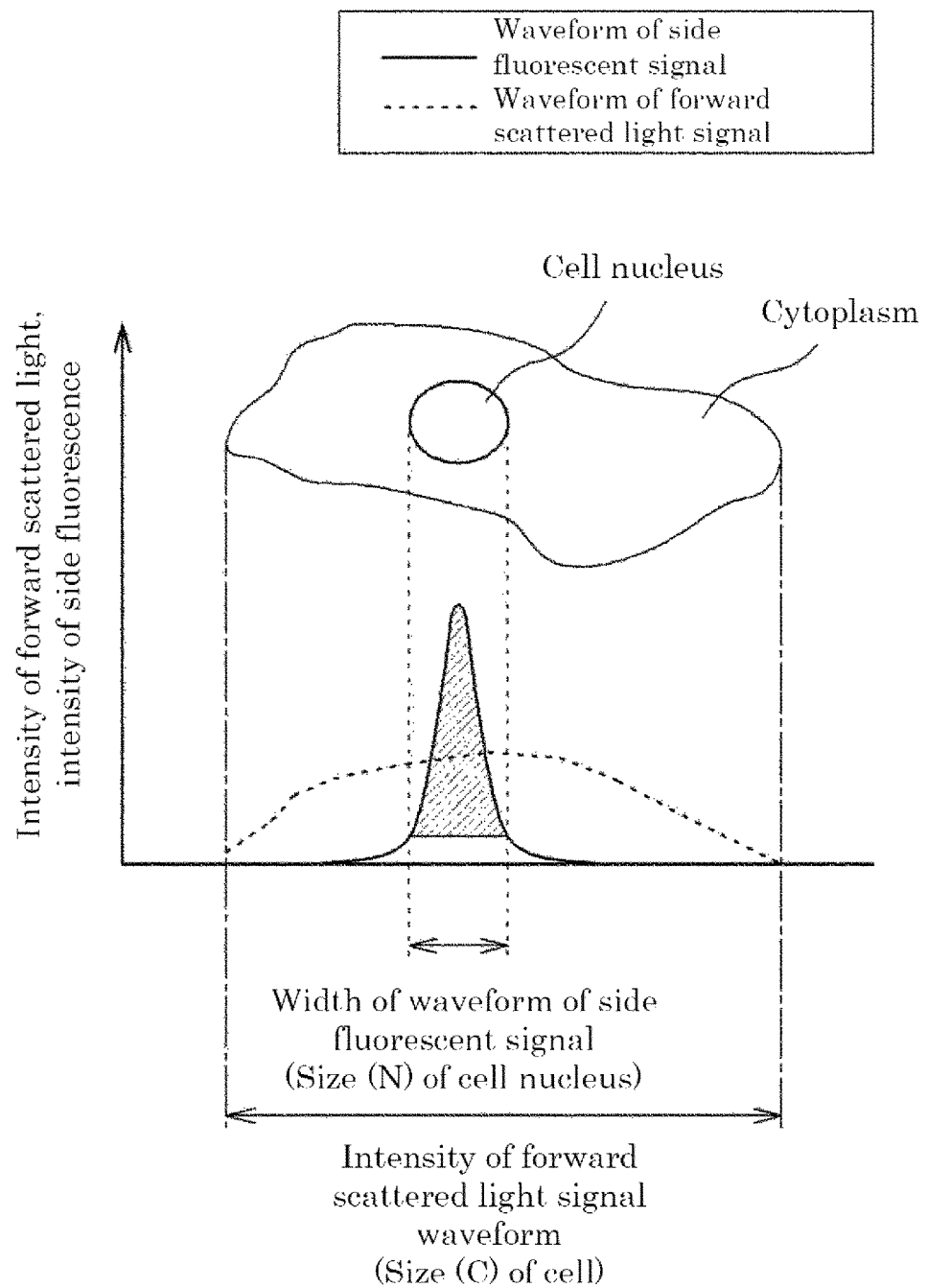
FIG. 6 is an explanatory view of measurement data.

FIG. 6 is an explanatory view of the measurement data to be obtained in Step S2. FIG. 6 shows a pattern diagram of a cell containing a nucleus, the waveform of the forward scattered light signal obtained from the cell, and the waveform of the side fluorescent signal. In FIG. 6, a vertical axis of the graph represents an intensity of each light. The width of the waveform of the forward scattered light intensity represents the numerical value indicating the width of cytoplasm (the second data pertaining to the size of cytoplasm). The width of the waveform of the side fluorescent intensity represents the numerical value indicating the width of the cell nucleus (the first data pertaining to the size of the cell nucleus). In FIG. 6, the hatched area, which is surrounded by the waveform of the side fluorescent intensity and a predetermined baseline, represents the amount of DNA of the cell. The CPU 27a calculates the N/C ratio in the cells which is a ratio of the first data and the second data, i.e., a ratio of the size of the cell nucleus and the size of the cell (=a ratio of the width of the side fluorescent signal waveform and the width of the forward scattered light signal waveform).

After Step S2, the microprocessor 20 transmits the measurement data including the forward scattered light data, side scattered light data, side fluorescence data, and characteristic parameter obtained in Step S2 to the data processing device 4 via the external communication controller 25 (Step S3) and terminates the processing.

Subsequently, the CPU 27a determines whether or not the measurement data is received from the microprocessor 20 (Step S4). In Step S4, when the CPU 27a determines that the measurement data is not received from the microprocessor 20 (No in Step S4), the CPU 27a repeats the processing of Step S4 until the data is received. On the other hand, in Step S4, when the CPU 27a determines that the measurement data is received from the microprocessor 20 (Yes in Step S4), the CPU 27a advances the processing to Step S5.

Figure 7:
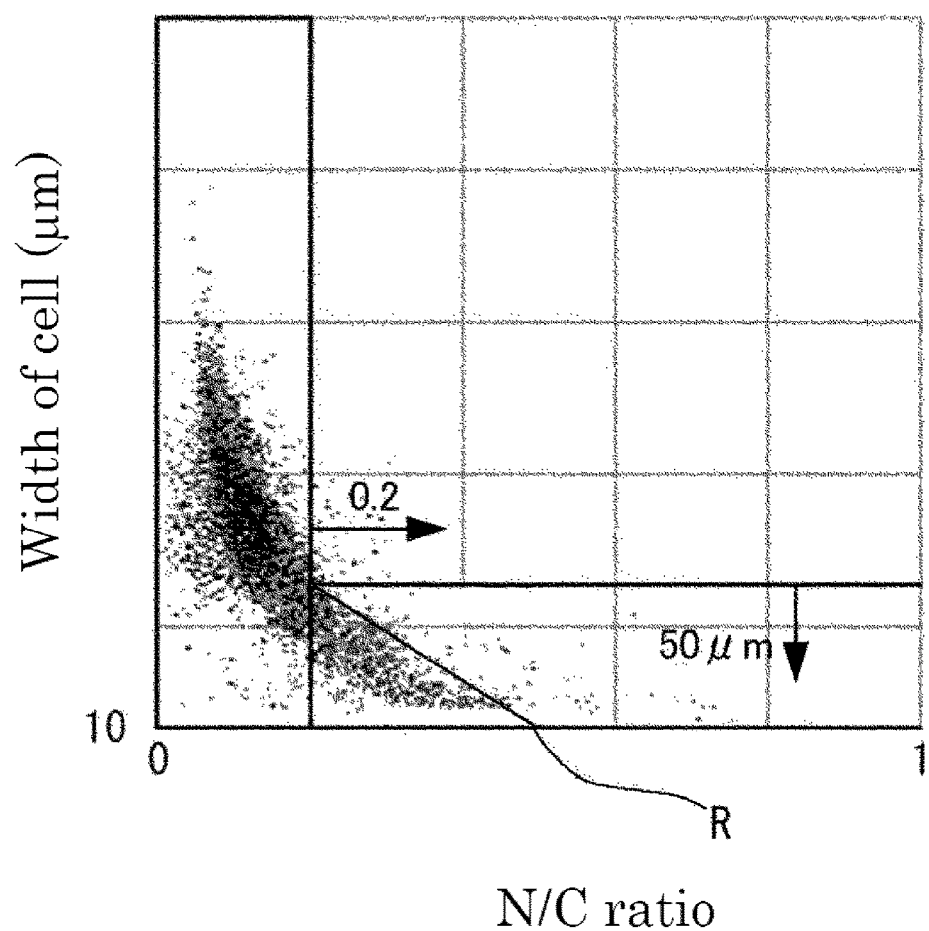
FIG. 7 is a view showing an example of the scattergram.

In Step S5, the CPU 27a creates a scattergram as shown in FIG. 7. The created scattergram can be displayed on the display unit 28 of the data processing device 4. The vertical axis of the scattergram represents the size of the cell, and the horizontal axis represents the N/C ratio. When epithelial cells of the uterine cervix collected from a normal person are analyzed by the canceration information providing device 1, the scattergram created in Step S5 is distributed so as to form a crescent shape from top left to bottom right as shown in FIG. 7.

Then, when the scattergram is created in Step S5, the CPU 27a determines whether or not more than or equal to 5000 (the fourth threshold) of single epithelial cells are present in the cells in the obtained measurement data in Step S6. In the present embodiment, the determination is performed by the following method described in US Patent Application publication No. 2008/0108103.

That is, it can be performed using the characteristic parameter B (difference integrated value/peak value) or the characteristic parameter M normalized secondary moment, which are obtained from the waveform signal of the forward scattered light. The A/D converter (not shown) samples a waveform signal, for example, at time points X0, X1, X2, . . . and Xn at sampling intervals of 20 nsec, and quantizes measured voltages with a resolution of 8 bits between a maximum voltage of 10 V and a baseline voltage of 0.05 V to convert the measured voltages into digital signals.

The characteristic parameter B is represented by Equation (1) below.

[Equation 1]

$$B \equiv \sum_{i=1}^{n} (\max(x_i, x_{i-1}) - \min(x_i, x_{i-1})) \div \text{Peak} \quad (1)$$

Here, the difference integrated value is a cumulative sum of absolute values of differences between neighboring sampling data, the peak value (Peak) indicates the maximum value of the waveform (refer to FIG. 8), and is represented by Equation (2) below.

[Equation 2]

$$\text{Peak} \equiv \max_{0 \leq i \leq n}(x_i) \quad (2)$$

The characteristic parameter M is represented by Equation (3) below.

Figure 8:
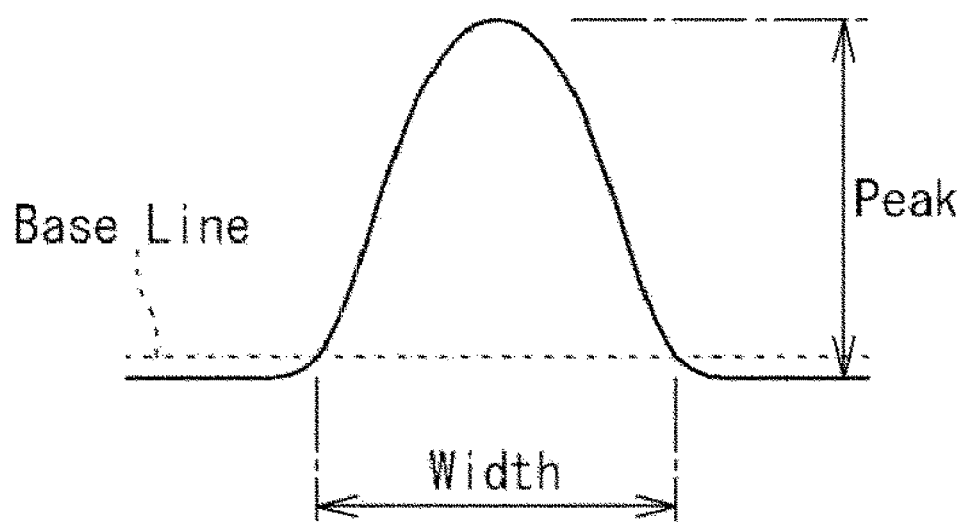
FIG. 8 is an explanatory view showing a relationship between signal waveform and characteristic parameter.

[Equation 3]

$$M \equiv \frac{\sum_{i=0}^{n} (\max(x_i, 0) \cdot (p-i)^2)}{\text{Peak} \cdot \text{Width}^2} \quad (3)$$

wherein P is a suffix which means that Xp is the peak value, the Width indicates the width of a portion of the waveform above the base line as shown in FIG. 8, and is represented by Equation (4) below.

[Equation 4]

$$\text{Width} \equiv \operatorname*{argmax}_{p \leq i \leq n}(x_i; x_i > BaseLine) - \operatorname*{argmin}_{p \leq i < p}(x_i; x_i > BaseLine) \quad (4)$$

wherein P is a suffix which means that Xp is the peak value. A threshold for determining whether or not a cell is a single cell is set according to experiments of the parameters. In the present embodiment, for example, the characteristic parameter B is used. When the characteristic parameter B is more than or equal to 2.2, the cell is determined as the aggregating cell. When the characteristic parameter B is less than 2.2, the cell is determined as the single cell. In the case of using the characteristic parameter M, when the characteristic parameter M is more than or equal to 2100, the cell is determined as the aggregating cell, when the characteristic parameter M is less than 2100, the cell is determined as the single cell.

The number (threshold) of "5000" described above is the number to be generally used as an indicator that determines the appropriateness of cytological diagnosis. In the present embodiment, the number of "5000" is employed as the threshold to ensure the analysis accuracy.

Figure 9:
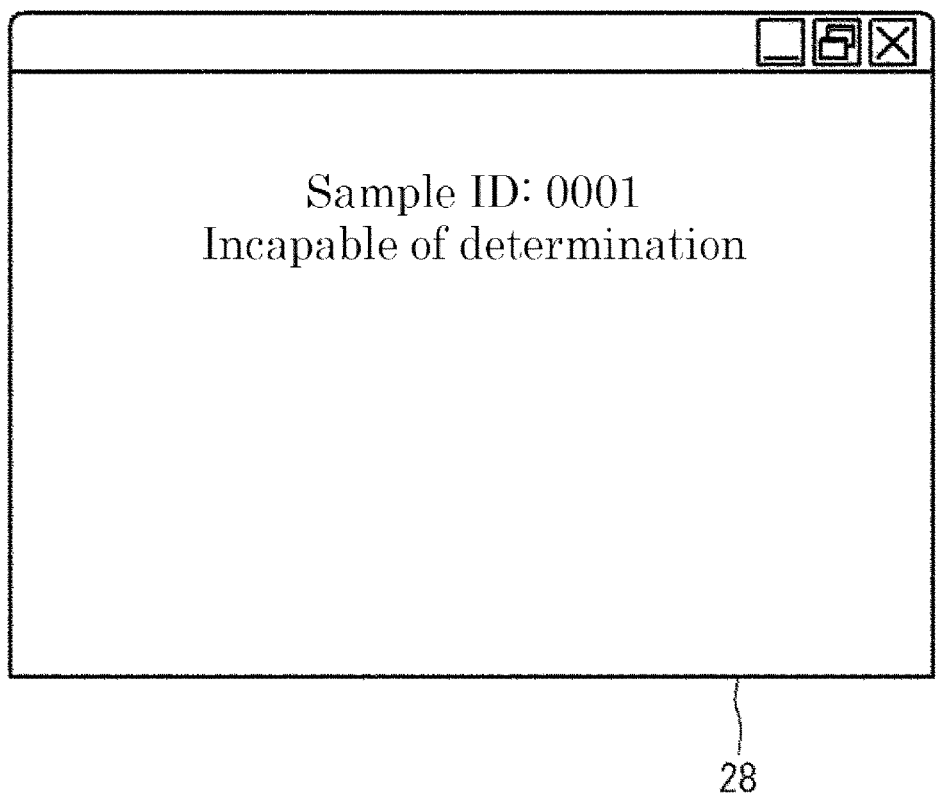
FIG. 9 is a view showing a display example of a display unit of the data processing device.

In Step S6, when the number of single cells is determined to be less than 5000, the CPU 27a does not extract the cells to be analyzed in Step S7 to be described below and proceeds to Step S13. In Step S13, the CPU 27a allows information incapable of determining the measurement sample prepared in Step S1 to be displayed on the display unit 28 as shown in FIG. 9 (Step S13).

In Step S6, when the number of single cells is determined to be more than or equal to 5000, the CPU 27a extracts measurement data of the cells to be analyzed using two parameters such as the size of the cell and the N/C ratio (Step S7).

[Extraction of Measurement Data of Cells to be Analyzed (Step S7)]

In epithelial tissues of the uterine cervix and oral mucosa which are mainly analyzed by the canceration information providing method and the device of the present invention, a plurality of kinds of cells exist in the form of a layer in order from the basal membrane. In the present specification, when the basement membrane is used as a lower layer, the side located at the upper layer indicates the surface layer side. In the uterine cervix and oral mucosa, the side adjacent to the outside corresponds to the surface layer side.

Figure 10:
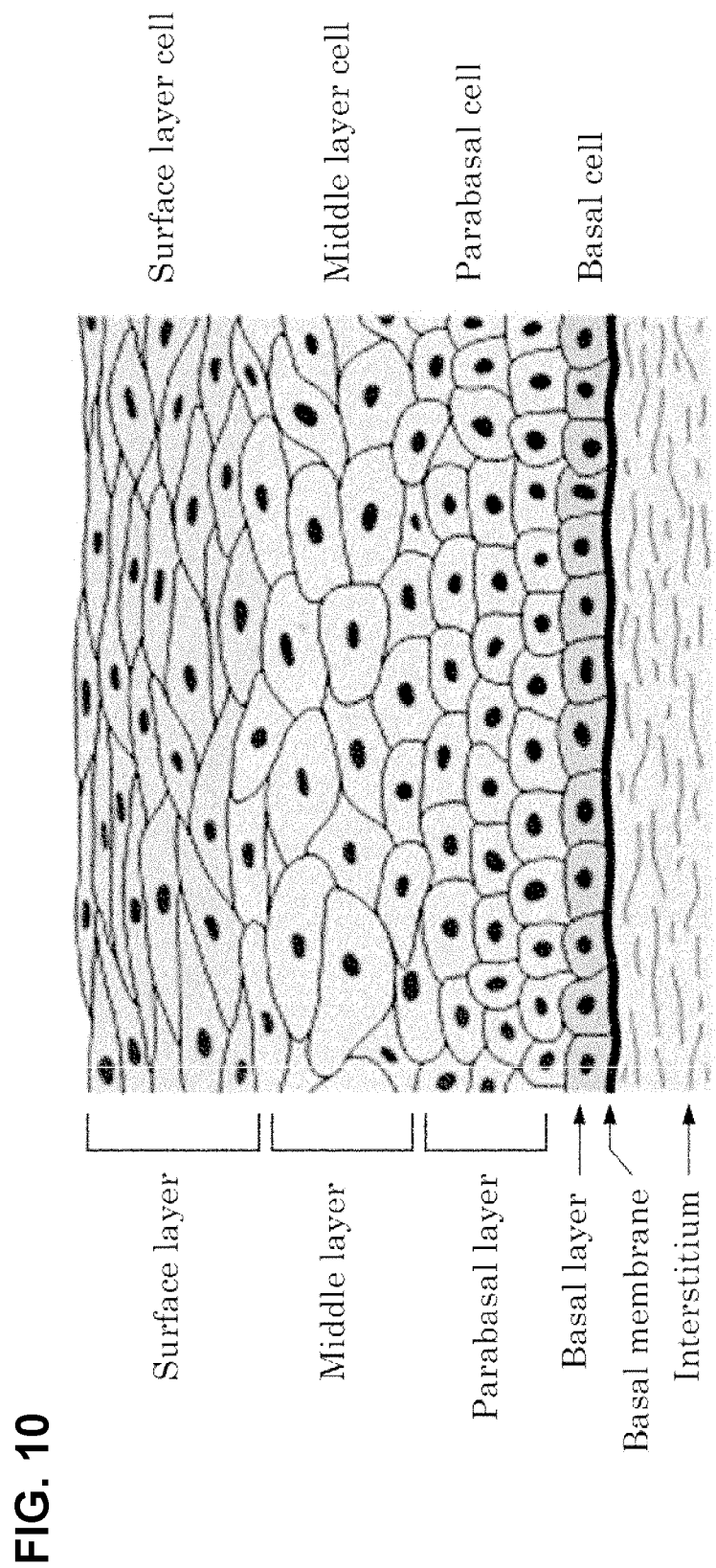
FIG. 10 is a pattern diagram of epithelial cells of the uterine cervix.

In the uterine cervix, as shown in FIG. 10, a layer (basal layer) formed by the basal cell, a layer (parabasal layer) formed by the parabasal cell, a layer (middle layer) formed by the middle layer cell, and a layer (surface layer) formed by the surface layer cell are formed in this order from the basal membrane side. The basal cell near the basal membrane is differentiated to the parabasal cell, the parabasal cell is differentiated to the middle layer cell, and the middle layer cell is differentiated to the surface layer cell. In the oral mucosa, the basal cell layer, the prickle cell layer, the granule cell layer, and the horny layer are formed in this order from the basal membrane side. These are summarized in Table 1 below.

TABLE 1

| | Name of cell | | N/C ratio | |
|---|---|---|---|---|
| | Squamous epithelium of uterine cervix | Epithelium of oral mucosa | Squamous epithelium of uterine cervix | Epithelium of oral mucosa |
| Surface layer side | Surface layer cell Middle layer cell | Horny layer Granule cell | Low | Low |
| Basal membrane side | Parabasal cell Basal cell | Prickle cell Basal cell | High | High |

As described above, the cell pertaining to the canceration of a plurality of kinds of cells in the epithelial tissue is the basal cell in the epithelial tissue of the uterine cervix, and it is the basal cell in the epithelial tissue of the oral mucosa. In the process of becoming a cancer, the basal cell acquires the atypical formation and becomes the atypical cell. The atypical cell acquires the ability to proliferate, and occupies from the basal layer side to the surface layer side. Thus, in the initial stage to becoming a cancer, a great number of cancerous cells exist in the cells existing in the basal layer, the parabasal layer, and the middle layer in the epidermal tissue of the uterine cervix. In the epithelial tissue of the oral mucosa, a great number of cancerous cells exist in the cells existing in the basal cell layer and the prickle cell layer. In contrast, in the initial stage to becoming a cancer, the cancerous cells are extremely few in the cells existing on the surface layer side of the epithelial tissue, such as the surface layer of the epithelial tissue of the uterine cervix and the horny layer of the epithelial tissue of the oral mucosa.

It is found that, in the epithelial tissue described above, the size of the cell sequentially becomes smaller but the size of the cell nucleus sequentially becomes larger from the layer on the surface layer side toward the layer on the basal membrane side. Therefore, the N/C ratio of the size of the cell nucleus with respect to the size of the cell also sequentially becomes larger from the layer on the surface layer side toward the layer on the basal membrane side. In the present embodiment, the measurement data of the cells to be analyzed is extracted using the size of the cell and the N/C ratio. Specifically, in Step S7, the measurement data in which the size of the cell is within a range of 10 to 50 μm and the N/C ratio is within a range of 0.2 to 1 is extracted.

Figure 11:
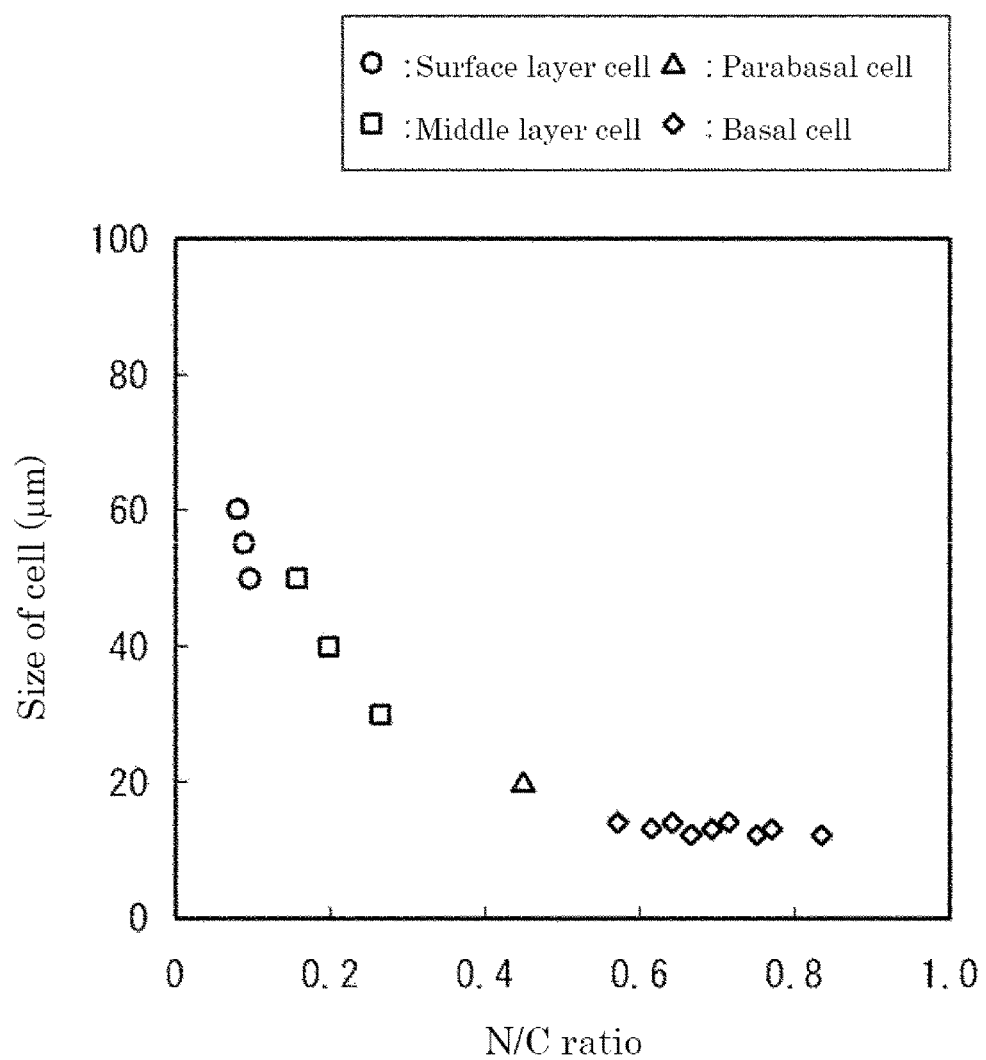
FIG. 11 is a view showing a relationship between the size of the cells and the N/C ratio as for various epithelial cells of the uterine cervix.

The size of the cell (the second threshold value) and the N/C ratio (the first threshold value) which become the criteria to determine whether or not the cells are extracted as the cells to be analyzed can be set for the observation and analysis of sample tissues according to the kind of the epithelial tissues to be analyzed. For example, in the case of screening of uterine cervix carcinoma using the epithelial tissue of the uterine cervix as the tissue to be analyzed, the determination criteria in which the N/C ratio is more than or equal to 0.2 and the cell width (the size of the cell) is less than or equal to 50 μm can be used. The form and size of cells forming the epithelial tissue of the uterine cervix and the nucleus size are summarized in Table 2 below. FIG. 11 shows the cells plotted in the coordinates where the horizontal axis represents the N/C ratio, and the vertical axis represents the size of the cell.

TABLE 2

| Name | Cell form | Size of cytoplasm | Size of nucleus |
| --- | --- | --- | --- |
| Surface layer cell | Polygonal | 50-60 μm | 5 μm |
| Middle layer cell | Polygonal to oval type | 30-50 μm | 8 μm |
| Parabasal cell | Oval type | 20 μm | 9 μm |
| Basal cell | Round to oval type | 12-14 μm | 8-10 μm |

In FIG. 11 and Table 2, it is found that, in the case of the epithelial tissue of the uterine cervix, the cells having an N/C ratio of less than or equal to 0.2 and a cell width of less than or equal to 50 μm are extracted so as to exclude almost the surface layer cells existing in the surface layer in which the cancerous cells are extremely few from the cells to be analyzed, and the middle layer cell, parabasal cell, and basal cell existing in the layer where a great number of cancerous cells exist as compared to the surface layer are obtained as the cells to be analyzed. In FIG. 11, a percentage of the surface layer cell in the total number of the cells is small for easier comprehension. However, the number of the surface layer cell in the epithelial tissue of the uterine cervix actually collected from a subject is higher than that of other cells. Therefore, when all the collected cells are used as the cells to be analyzed, even if the cancerous cells are included in the cells, their presence is diluted. It is considered that it is not determined as necessary for the reexamination (positive). That is, when all the collected cells are used as the cells to be analyzed, it is difficult to improve the detection sensitivity.

However, the surface layer cells existing in the surface layer in which the cancerous cells are extremely few are excluded from the collected cells so as to substantially exclude them from the cells to be analyzed. Thus, it is possible to increase a percentage of the cancerous cells in the total number of the cells. As a result, the detection sensitivity of the cancerous cells can be improved.

In the canceration information providing method of the present invention, in the step of extracting the cell for extracting the measurement data of the cells to be analyzed, the cells having a certain high level of the N/C ratio which includes the cells existing in the layer near the basal membrane are extracted. Since there are variations in the size and N/C ratio of the cell, it is actually impossible to exclude only all the surface layer cells from the cells to be analyzed in the above extraction method. Some of the surface layer cells may be extracted as the cells to be analyzed. In contrast, some of the middle layer cell, parabasal cell, and basal cell may be excluded from the cells to be analyzed. However, the size and N/C ratio of the cell (as the determination criteria for extraction) are appropriately selected so that almost the surface layer cells having a high possibility of being the cancerous cell can be excluded from the cells to be analyzed.

In the present invention, for example, in the uterine cervix, the basal cell, parabasal cell, and middle layer cell are extracted from the cell population of the basal cell, parabasal cell, middle layer cell, and surface layer cell. In the oral mucosa, the basal cell and prickle cell are extracted from the cell population of the basal cell, prickle cell, granule cell, and horny cell.

Returning to the flow chart of FIG. 5, in Step S7, the CPU 27a extracts the measurement data of the cells having an N/C ratio of more than or equal to 0.2 and a cell width of less than or equal to 50 μm. Then, in Step S8, the CPU 27a determines whether or not the number of the cells having an N/C ratio of more than or equal to 0.2 and a cell width of less than or equal to 50 μm is more than or equal to 1000 (the third threshold). When the CPU 27a determines that the number of the cells having an N/C ratio of more than or equal to 0.2 and a cell width of less than or equal to 50 μm is more than or equal to 1000 (Yes in Step S8), the CPU 27a proceeds the processing to Step S9 and creates a histogram to be described below (a histogram of the amount of DNA) in Step S9. On the other hand, when the CPU 27a determines that the number of the cells having an N/C ratio of more than or equal to 0.2 and a cell width of less than or equal to 50 μm is less than 1000 in Step S8 (No in Step S8), the CPU 27a does not perform Steps S11 and S12 to be described below and proceeds to Step S13. In Step S13, the CPU 27a displays information incapable of determining the measurement sample prepared in Step S1 on the display unit 28 as shown in FIG. 9 (Step S13). The value (the third threshold) of 1000 is a value selected by various kinds of experiments and verifications, taking into consideration the analytic accuracy and reliability, and it is not particularly limited in the present invention.

Figure 12:
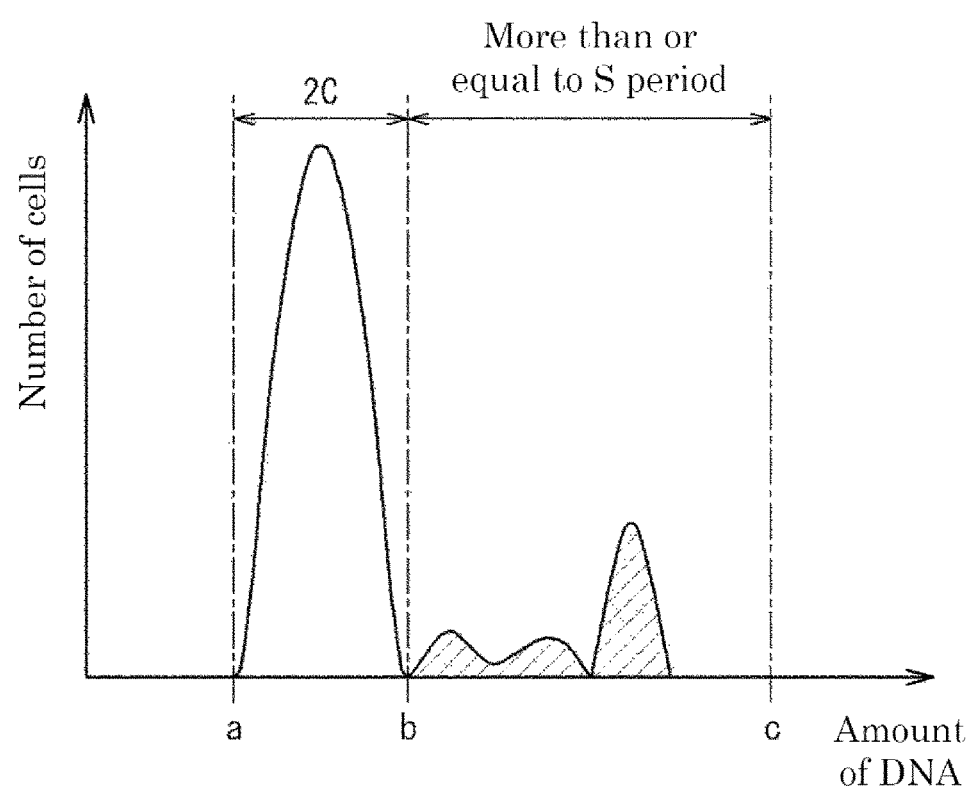
FIG. 12 is a histogram of the amount of DNA in the extracted cells.

FIG. 12 shows an example of the histogram to be created in Step S9. FIG. 12 shows the histogram created for the cells having an N/C ratio of more than or equal to 0.2 and a cell width of less than or equal to 50 μm which are extracted in Step S7. The vertical axis represents the number of cells, and the horizontal axis represents the amount of DNA of cells. The range indicating the normal amount of DNA (hereinafter referred to as "2C") is calculated from the data of many negative samples. In this embodiment, the range indicating the normal amount of DNA is set to the range from a to b. The range of the abnormal amount of DNA (hereinafter referred to as "more than or equal to the S period") is set to the range greater than the normal amount of DNA, and is set to the range greater than b and less than or equal to c. The range of the normal amount of DNA and the range of the abnormal amount of DNA are not particularly limited in the present invention, and they are values selected by various kinds of experiments and verifications, taking into consideration the analytic accuracy and reliability.

Figure 13:
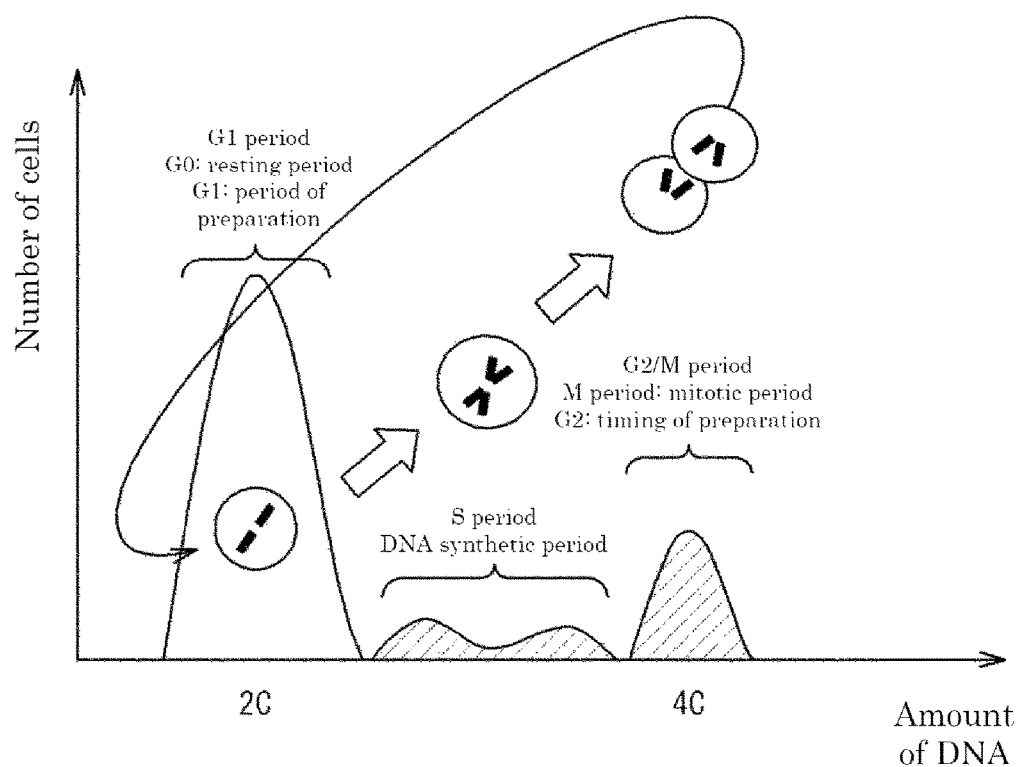
FIG. 13 is a view for explaining the cell cycle in relation to the histogram of the amount of DNA.

The cell becomes two cells and returns to the starting point through events such as DNA replication, distribution of chromosome, nuclear division, and cytoplasmic division according to a certain cycle (cell cycle) as described in FIG. 13. The cell cycle can be divided to the following four periods according to the stage. If G0 period (resting period)

in which the proliferation of the cell is resting is added to the four periods, the cell is in one of the stages of the five periods. G1 period (timing of preparation and inspection to enter S period): S period (DNA synthetic period); G2 period (timing of preparation and inspection to enter M period); and M period (mitotic period).

Figure 14:
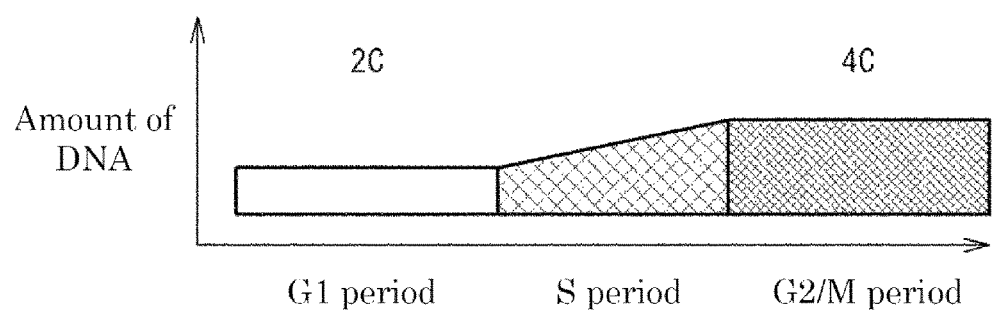
FIG. 14 is a view for explaining a relationship between stages in the cell cycle and the amounts of DNA.

When the cell proliferates according to the cell cycle, the chromosome of the nucleus in the cell also increases, and hence what state of the cell cycle the cell is in can be estimated by measuring the amount of DNA of the cell. In the case of a normal cell, the amount of DNA in the G1 period is a constant value, the amount of DNA gradually increases in the following S period, the amount of DNA is a constant value in the G2 period, and such value is maintained in the M period, as shown in FIG. 14. When a histogram of the amount of DNA is created for the normal cell, a histogram shown in FIG. 13 is obtained. A hill having the highest peak corresponds to the cell in the G0 or G1 period in which the amount of DNA is the least, a hill having the second highest peak corresponds to the cell in the G2 or M period in which the amount of DNA is the largest, and a period therebetween corresponds to the cell in the S period.

In the case of normal cells, a ratio of the number of cells in the state of the S period, the G2 or M period and the number of cells in the G0 or G1 period is a value within a constant range. However, in the case of cancerous cells or cells in the process of canceration, the number of chromosomes of the cell abnormally increases, and hence the amount of DNA increases. Since the ability to proliferate in the cancerous cells is higher than that in the normal cells, the number of the cell having a large amount of DNA increases.

The number of the normal cell in the G0 period or the G1 period is used as the criterion, and a ratio of the number of the cell having the amount of DNA higher than the amount of DNA of the normal cell with respect to this cell number is used as the determination criterion so that it is possible to estimate whether or not the cells to be analyzed are cancerous cells. Specifically, in the histogram of the amount of DNA shown in FIG. 12, the hill at the leftmost side corresponds to the normal cell in the G0 period or the G1 period in which the amount of DNA is low, and the three hills at the right side correspond to the cell having the amount of DNA higher than the amount of DNA of the normal cell in the G0 period or the G1 period. The three hills at the right side are considered to correspond to the cell in the S period shown in FIG. 13 (the two hills at the center) or the cell in the G2/M period (the hill at the rightmost side). If the cancerous cells are included in the cells to be analyzed, the cancerous cells are also included in the two hills. The number of cancerous cells increases, and hence the three hills are considered to become higher. In FIG. 12, the example with the three hills is illustrated for easier comprehension. When a histogram of the amount of DNA in the epithelial tissue of the uterine cervix actually collected from a subject is created, the formation of the hills depends on the subject's condition.

Then, the ratio to be used as the determination criterion can be selected by performing the experiment and verification using a plurality of clinical samples containing positive and negative samples. In the present embodiment, from the viewpoint of obtaining sensitivity of more than or equal to 90%, the determination criterion is whether or not the ratio of the number of the cell having the amount of DNA higher than the amount of DNA of the normal cell (the cell in the range indicating the abnormal amount of DNA) with respect to the number of the normal cell in the G0 period or the G1 period (the cell in the range indicating the normal amount of DNA) is more than or equal to 16% (the fifth threshold).

That is, a cutoff value for determining whether a reexamination of the sample is necessary (positive) or the reexamination is not necessary (negative) is set to 16%. The cutoff value (16%) is not particularly limited in the present invention. It can be appropriately set, taking into consideration a balance between the sensitivity of the clinical test and the specificity.

Figure 15:
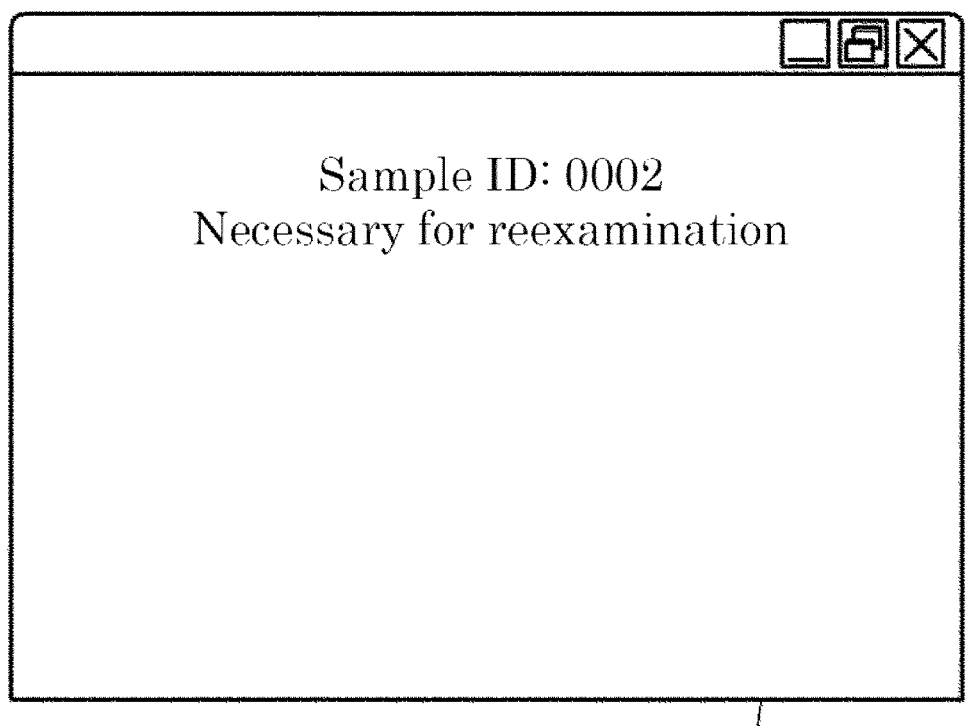
FIG. 15 is a view showing a display example of the display unit of the data processing device.
Figure 16:
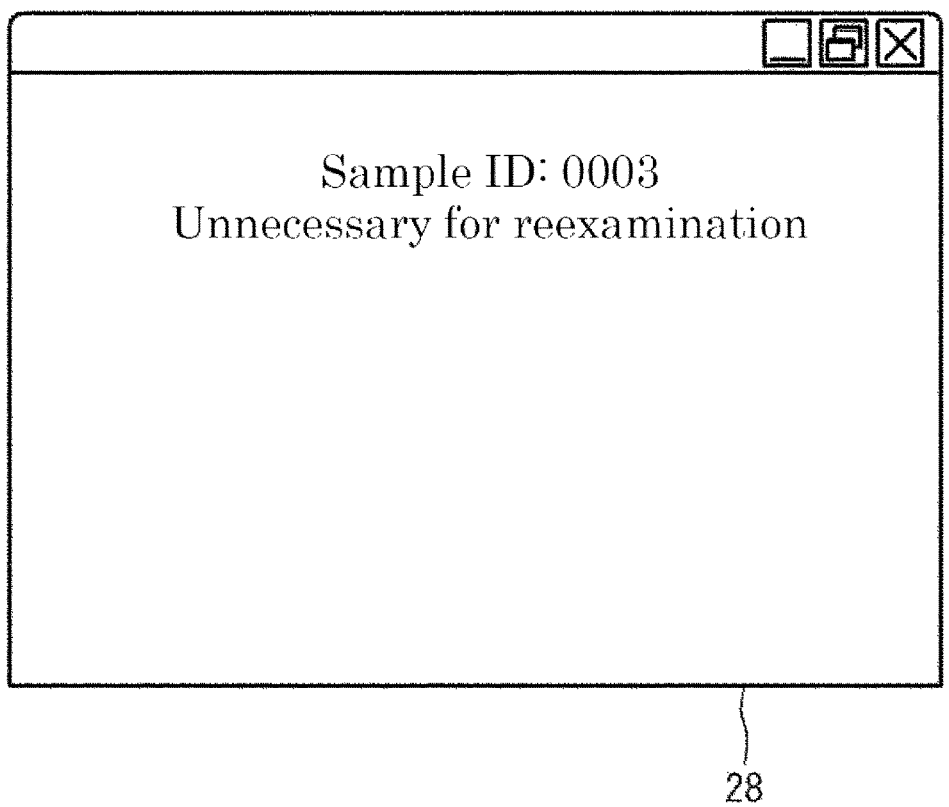
FIG. 16 is a view showing a display example of the display unit of the data processing device.

In Step S10, when a ratio of the number of the cell having the amount of DNA higher than the amount of DNA of the normal cell (second group) with respect to the number of the cell in the range indicating the normal amount of DNA (first group) is determined to be more than or equal to 16% (Yes in Step S10), the measurement sample used for analysis is determined as necessary for the reexamination (positive) in Step S11. The result is displayed on the display unit 28 of the data processing device 4 as shown in FIG. 15. On the other hand, in Step S10, when the ratio is determined to be less than 16% (No in Step S10), the measurement sample used for analysis is determined as unnecessary for the reexamination (negative) in Step S12. The result is displayed on the display unit 28 of the data processing device 4 as shown in FIG. 16.

Figure 17:
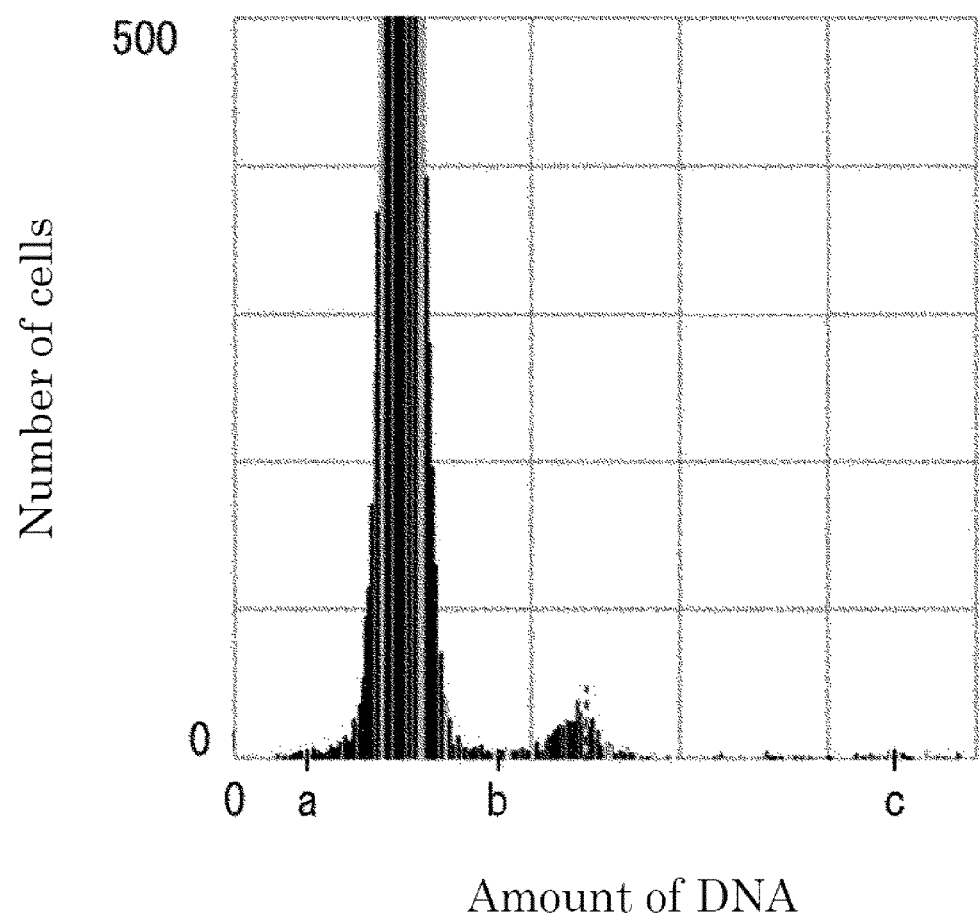
FIG. 17 is a view showing an example of the created histogram of all single cells.

FIG. 17 is a histogram created when the cells collected from the epithelial tissue of the uterine cervix of a subject of CIN3 (state diagnosed as the initial stage to becoming a cancer in the tissue diagnosis) are analyzed in the device which creates a histogram of the amount of DNA of all the single epithelial cells without executing extraction of measurement data of cells to be analyzed (Step S7) and Step S8 and creates a histogram of the amount of DNA of all the single epithelial cells, in the canceration information providing device 1 according to one embodiment of the present invention.

Figure 18:
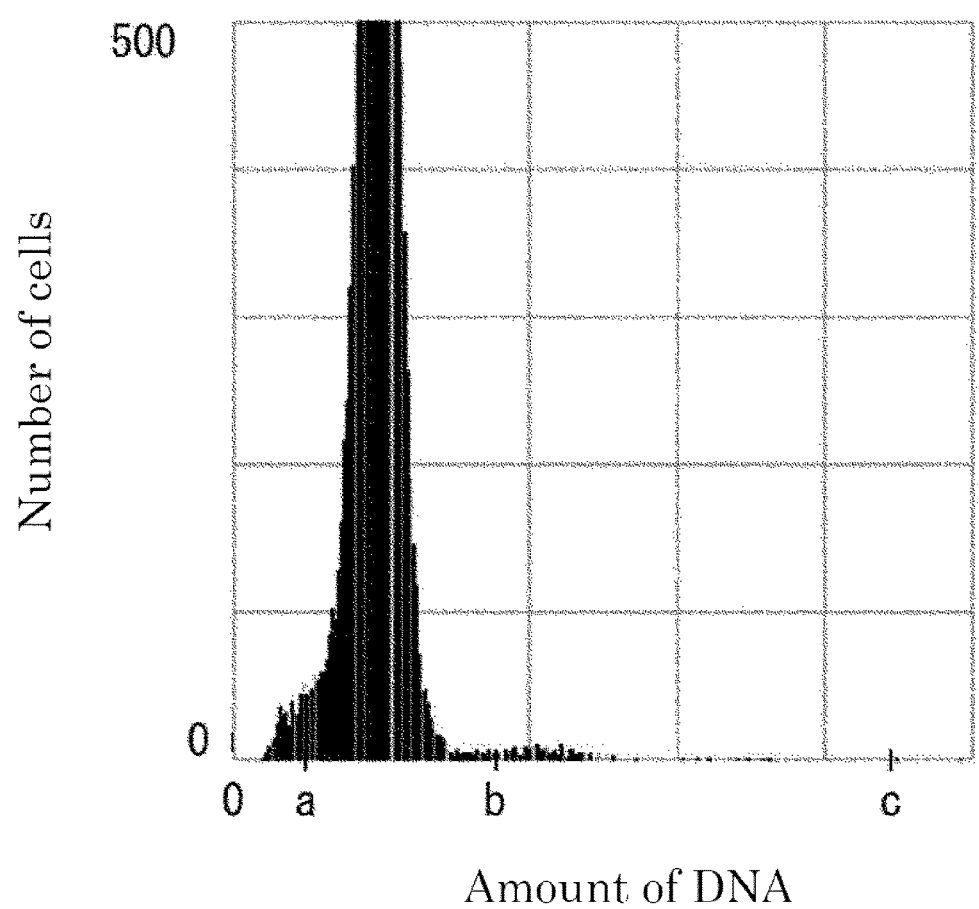
FIG. 18 is a view showing another example of the created histogram of all single cells.

FIG. 18 is a histogram created when the cells collected from the epithelial tissue of the uterine cervix of a subject of NILM (state diagnosed as Normal in the cytological diagnosis) are analyzed in the device which creates a histogram of the amount of DNA of all the single epithelial cells without executing extraction of measurement data of cells to be analyzed (Step S7) and Step S8 and creates a histogram of the amount of DNA of all the single epithelial cells, in the canceration information providing device 1 according to one embodiment of the present invention.

Figure 19:
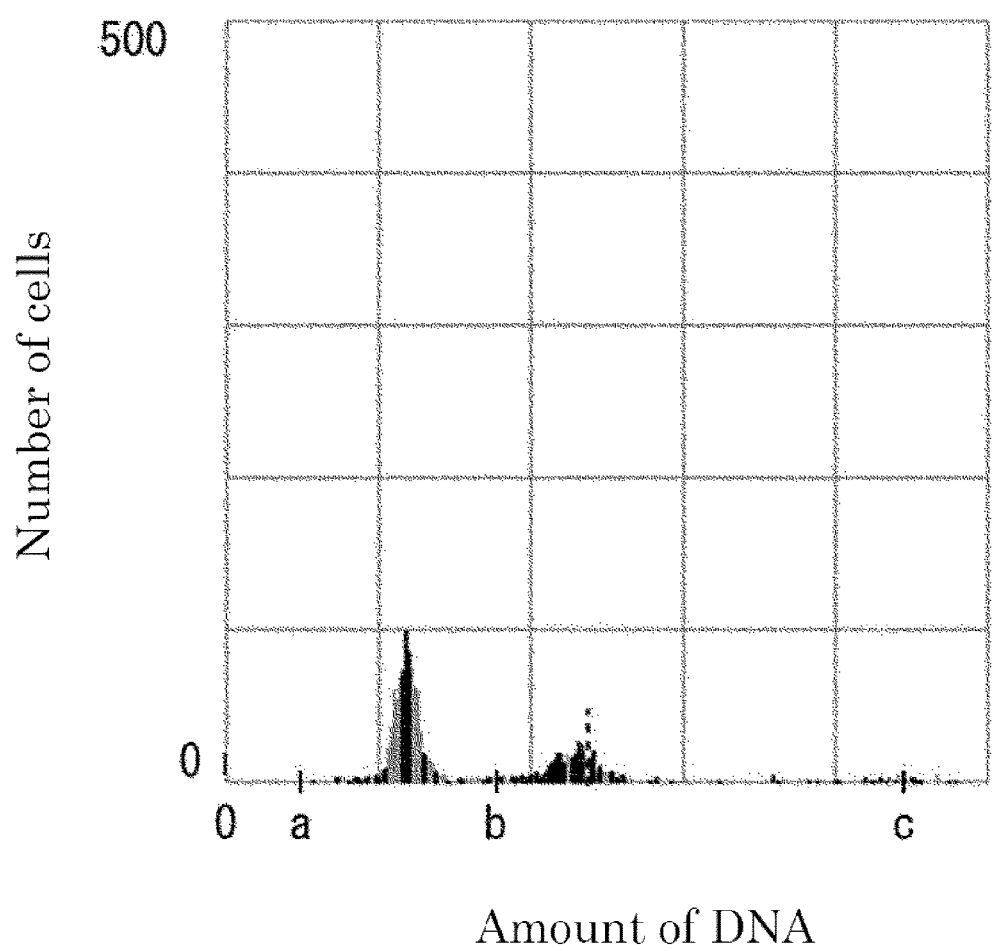
FIG. 19 is a view showing an example of the histogram to be created in Step S9.
Figure 20:
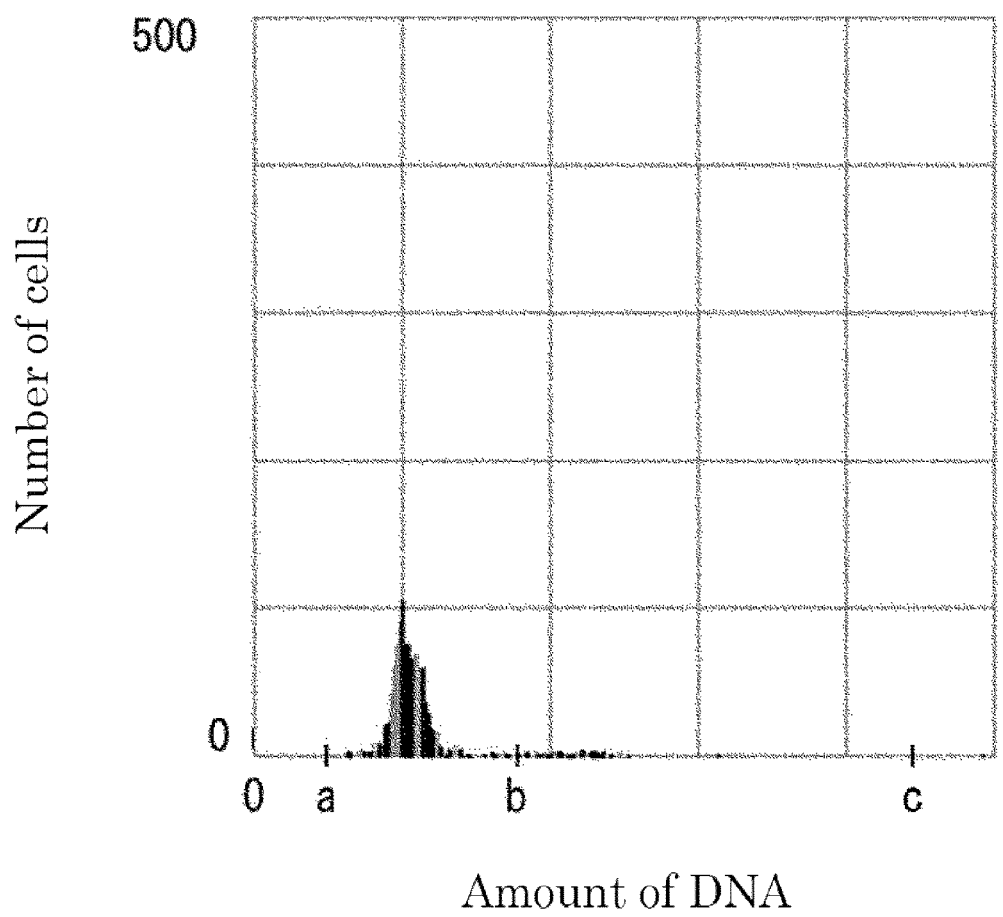
FIG. 20 is a view showing another example of the histogram to be created in Step S9.

FIG. 19 is a histogram created in Step S9 when the cells collected from the epithelial tissue of the uterine cervix of a subject of CIN3 (state diagnosed as the initial stage to becoming a cancer in the tissue diagnosis) are analyzed, in the canceration information providing device 1 according to one embodiment of the present invention. FIG. 20 is a histogram created in Step S9 when the cells collected from the epithelial tissue of the uterine cervix of a subject of NILM (state diagnosed as Normal in the cytological diagnosis) are analyzed, in the canceration information providing device 1 according to one embodiment of the present invention.

When the number of the cell having the amount of DNA higher than the amount of DNA of the normal cell (more than or equal to the S period) with respect to the number of the cell in the range (2C) indicating the normal amount of DNA is calculated based on the histogram of FIG. 17, it is 3.2%. When the number of the cell having the amount of DNA higher than the amount of DNA of the normal cell (more than or equal to the S period) with respect to the number of the cell in the range (2C) indicating the normal amount of DNA is calculated based on the histogram of FIG. 18, it is 1.1%. This shows that, when a histogram of the amount of DNA of all the single epithelial cells is created without executing extraction of measurement data of cells to be analyzed (Step S7) and Step S8, it is unlikely to result in a large difference between the subject of CIN3 and the subject of NILM in the ratio the number of the cell having the amount of DNA higher than the amount of DNA of the normal cell (more than or equal to the S period) with respect to the number of the cell in the range (2C) indicating the normal amount of DNA.

On the other hand, when the number of the cell having the amount of DNA higher than the amount of DNA of the normal cell (more than or equal to the S period) with respect to the number of the cell in the range (2C) indicating the normal amount of DNA is calculated based on the histogram of FIG. 19, it is 57.9%. When the number of the cell having the amount of DNA higher than the amount of DNA of the normal cell (more than or equal to the S period) with respect to the number of the cell in the range (2C) indicating the normal amount of DNA is calculated based on the histogram of FIG. 20, it is 7.4%. This shows that, when extraction of measurement data of cells to be analyzed (Step S7) and Step S8 are executed to create a histogram of the amount of DNA, it is likely to result in a large difference between the subject of CIN3 and the subject of NILM in the ratio the number of the cell having the amount of DNA higher than the amount of DNA of the normal cell (more than or equal to the S period) with respect to the number of the cell in the range (2C) indicating the normal amount of DNA. When the cutoff value for determining whether a reexamination of the sample is necessary (positive) or the reexamination is not necessary (negative) is set to 16%, as described in the present invention, the subject of CIN3 is determined as necessary for the reexamination (positive), and the subject of NILM is determined as unnecessary for the reexamination (negative). The result agrees with the determination of tissue or cytological diagnosis.

[Other Modified Examples]

The disclosed embodiments are illustrative and not restrictive in all respects. The scope of the present invention is defined by the attached claims rather than by the embodiments, and all changes within the meaning and scope equivalent to the scope of claims are enclosed therein.

For example, in the embodiment described above, the width of the waveform of the forward scattered light intensity is obtained as the data reflecting the size of the cell. It may be the peak of the waveform of the forward scattered light intensity or the area of the region surrounded by the waveform of the forward scattered light intensity and a predetermined baseline. In the embodiment described above, the width of the waveform of the side fluorescence intensity is obtained as the data reflecting the size of the cell nucleus. It may be the peak of the waveform of the side fluorescence intensity or the area of the region surrounded by the waveform of the side fluorescence intensity and a predetermined baseline.

In the embodiment described above, when it is determined as "NO" in Step S6, the information incapable of determining it is output, and the processing of Step S11 and Step S12 is not performed. However, the present invention is not limited thereto. In the present invention, even when it is determined as "NO" in Step S6, the processing following Step S7 is executed, information of fewer cell number is added to the determination result to be output in Step S11 or Step S12, and the result can be output. In the embodiment described above, when it is determined as "NO" in Step S8, the information incapable of determining it is output, and the processing of Step S11 and Step S12 is not performed. However, the present invention is not limited thereto. In the present invention, even when it is determined as "NO" in Step S8, the processing following Step S9 is executed, information of fewer cell number is added to the determination result to be output in Step S11 or Step S12, and the result can be output.

In the embodiment described above, the width of the cell nucleus, the amount of DNA of the cell, and data corresponding to the width of the cytoplasm are obtained using the optical information obtained by the flow cytometer. The width of the cell nucleus, the amount of DNA of the cell, and data corresponding to the width of the cytoplasm can be obtained by analyzing the image of the cell captured by the image capturing unit.

In the embodiment described above, the histogram as shown in FIG. 12 is used and the ratio of the number of the cell having the amount of DNA higher than the amount of DNA of the normal cell with respect to the number of the normal cell in the G0 period or the G1 period is used as the determination criterion in order to analyze the extracted cells. Instead of the analysis using the histogram, the cells can be analyzed using the scattergram as shown in FIG. 7. Specifically, in the scattergram of FIG. 7, based on a ratio of the cells belonging to the region where the middle layer cell, parabasal cell, and basal cell appear (region surrounded by a triangle in a quadrangle in FIG. 7) to the cells belonging to the region where the cancerous cells appear (region excluding the triangular region in the quadrangle), the measurement sample can be determined as necessary for the reexamination (positive) or unnecessary for the reexamination (negative). The region in the quadrangle is a region where the cells extracted using parameters such as the size of the cell and the N/C ratio appear. In the above triangular region, a point R where the side of the triangle intersects the horizontal axis can be set by performing the experiment and verification using a plurality of clinical samples containing positive and negative samples. The region except the triangular region in the quadrangle is a region where the cells having an abnormally high amount of DNA appear. When the ratio of the cells belonging to this region is more than or equal to a predetermined value, the measurement sample can be determined as necessary for the reexamination (positive).

In the embodiment described above, the ratio of the width of the cell nucleus/the width of the cytoplasm is employed as the N/C ratio, and the ratio of the area of the cell nucleus/the area of the cytoplasm can be employed as the N/C ratio.

In the embodiment described above, in the process of extracting the cells to be analyzed, the middle layer cell, the parabasal cell, and the basal cell are extracted. However, the present invention is not limited thereto and it suffices that some of the cells located toward the basal layer side of the cells in the surface layer are contained. Specifically, for example, the parabasal cell and the basal cell may be extracted, the middle layer cell and the parabasal cell may be extracted, only the middle layer cell may be extracted, only the parabasal cell may be extracted, or only the basal cell may be extracted. In addition to the middle layer cell, a part of the surface layer cell may be included in the cell to be extracted.

In the embodiment described above, both the N/C ratio and the width of the cytoplasm are used as the parameters for extraction. However, only the N/C ratio can also be used as the parameter for extraction. In this case, the detection sensitivity of the cancerous cells is slightly reduced. The speed of analysis can be increased by excluding the width of the cytoplasm from the parameter for extraction. As shown in FIG. 7, when the horizontal axis represents the N/C ratio and the vertical axis represents the width of the cytoplasm, the cells in the measurement sample are distributed to form a crescent shape from top left to bottom right. Thus, the N/C ratio as the cutoff value is appropriately selected so that it is possible to extract the cells having almost the same number as that when both the N/C ratio and the width of the cytoplasm are used as the parameters.

In the embodiments described above, the epithelial cells of the uterine cervix are used as the cells to be analyzed, and cells at other sites, such as the oral cavity can be used as the cells to be analyzed.

What is claimed is:

1. A method for providing information pertaining to canceration of cells using a cell analyzer, the method comprising:
    flowing, through a flow cell, a measurement specimen including cells collected from cervical or oral mucosa epithelial tissue;
    irradiating the measurement specimen flowing through the flow cell with light;
    detecting a scattered light and a fluorescence from each of the cells and outputting a scattered light signal and a fluorescence signal;
    acquiring, for each of the cells, a cell nucleus size from the fluorescence signal, a cell size from the scattered light signal, and an amount of DNA from the fluorescence signal;
    calculating a first ratio of the cell nucleus size and the cell size for each cell contained in the measurement specimen;
    extracting measurement data of target cells comprising at least some of the cells located toward a basal membrane side of cells existing in a surface layer in the epithelial tissue from the measurement data of the cells in the measurement specimen by comparing the first ratio with a first threshold value so as to substantially exclude data of the surface layer cells existing in the surface layer, the extracted measurement data including the cell nucleus size, the cell size and the amount of DNA for the target cells; and
    counting cells having an amount of DNA above a second threshold value based on the extracted measurement data; and
    outputting information pertaining to canceration of cells based on a number of cells having an amount of DNA above the second threshold value, wherein the information indicates at least one of whether a reexamination is necessary, and whether a subject is positive for cancer of the cervix or oral mucosa.

2. The method according to claim 1, wherein the cell nucleus size is a numerical value indicating the size of the cell nucleus, the cell size is a numerical value indicating the size of the cell.

3. The method according to claim 2, wherein the step of extracting the measurement data comprises extracting the measurement data of the target cells in which the first ratio is more than or equal to the first threshold value.

4. The method according to claim 2, wherein the step of extracting the measurement data comprises extracting the measurement data of the target cells based on the first ratio and the cell size.

5. The method according to claim 4, wherein the step of extracting the measurement data comprises extracting the measurement data of the target cells in which the cell size is less than or equal to a third threshold value.

6. The method according to claim 1, wherein the step of outputting the information further comprises:
    classifying the target cells into a first group in which a normal amount of DNA is indicated and a second group in which the amount of DNA is greater than a range indicating the normal amount of DNA;
    calculating a second ratio of a number of the target cells in the first group and a number of the target cells in the second group; and
    determining the information pertaining to the canceration of cells based on the second ratio.

7. The method according to claim 1, further comprising:
    comparing a number of the target cells with a fourth threshold value; and
    when the number of the target cells is less than the fourth threshold value, forbidding the output of the information pertaining to the canceration of cells, or outputting the information pertaining to the canceration of cells in addition to information indicating that a number of the cells is low.

8. The method according to claim 1, further comprising dispersing aggregating cells in the measurement specimen prior to the step of acquiring the measurement data.

9. The method according to claim 1, further comprising:
    comparing a number of single epithelial cells with a fifth threshold value; and
    when the number of single epithelial cells is less than the fifth threshold, value forbidding the output of the information pertaining to the canceration of cells, or outputting the information pertaining to the canceration of cells in addition to the information indicating a number of cells is low.

10. The method according to claim 1, wherein the cells comprise cells of the uterine cervix, and the cells existing in the surface layer comprise surface layer cells.

11. The method according to claim 1, wherein the step of outputting the information includes outputting the information pertaining to whether or not a reexamination is necessary.

12. A device for providing information pertaining to canceration of cells, the device comprising:
    a flow cell accommodating a flow of a measurement specimen including cells collected from cervical or oral mucosa epithelial tissue;
    an optical source configured to irradiate the measurement specimen flowing through the flow cell with light;
    a detector configured to detect a scattered light and a fluorescence from each of the cells and to output a scattered light signal and a fluorescence signal; and
    a processor programmed to:
    acquire, for each of the cells, a cell nucleus size from the fluorescence signal, a cell size from scattered light signal, and an amount of DNA from the fluorescence signal;
    calculate a ratio of the cell nucleus size and the cell size for each cell contained in the measurement specimen;
    extract measurement data of target cells comprising at least some of the cells located toward a basal membrane side of the cells existing in a surface layer in the epithelial tissue from the measurement data of the cells in the measurement specimen by comparing the calculated ratio with a first threshold value, so as to substantially exclude data of the surface layer cells existing in the surface layer and, the extracted measurement data including the cell nucleus size, the cell size and the amount of DNA for the target cells;
    count cells having an amount of DNA above a second threshold value based on the extracted measurement data; and output information pertaining to the canceration of cells based on a number of cells having an amount of DNA above the second threshold value, wherein the information indicates at least one of whether a reexamination is necessary, and whether a subject is positive for cancer of the cervix or oral mucosa.

13. The device according to claim 12, further comprising:
an image capturing unit that captures an image of the cells contained in the measurement specimen flowing through the flow cell,
wherein the cell nucleus size is an area of the cell nucleus in the image captured by the image capturing unit and the cell size is an area of the cells in the image captured by the image capturing unit.

14. The device according to claim 12, wherein the cell nucleus size is a numerical value indicating the size of the cell nucleus, the cell size is a numerical value indicating the size of the cell.

15. The device according to claim 14, wherein the processor is programmed to extract the measurement data of the target cells in which the calculated ratio is more than or equal to the first threshold value.

16. The device according to claim 15, wherein the processor is programmed to extract the measurement data of the target cells based on the calculated ratio and the cell size.

17. The device according to claim 16, wherein the processor is programmed to extract the measurement data of the target cells in which the cell size is less than or equal to a third threshold value.

18. The device according to claim 12, wherein the processor is programmed to output information pertaining to whether or not a reexamination is necessary.

* * * * *